United States Patent
Covey

(10) Patent No.: US 10,160,738 B2
(45) Date of Patent: *Dec. 25, 2018

(54) NEUROACTIVE SUBSTITUTED CYCLOPENT[A]ANTHRACENES AS MODULATORS FOR GABA TYPE-A RECEPTORS

(71) Applicant: Washington University, St. Louis, MO (US)

(72) Inventor: Douglas Covey, St. Louis, MO (US)

(73) Assignee: Washington University, St. Louis, MO (US)

(*) Notice: Subject to any disclaimer, the term of this patent is extended or adjusted under 35 U.S.C. 154(b) by 41 days.

This patent is subject to a terminal disclaimer.

(21) Appl. No.: 15/376,938

(22) Filed: Dec. 13, 2016

(65) Prior Publication Data

US 2017/0233356 A1 Aug. 17, 2017
US 2018/0086727 A9 Mar. 29, 2018

Related U.S. Application Data

(62) Division of application No. 14/203,678, filed on Mar. 11, 2014, now Pat. No. 9,562,026.

(60) Provisional application No. 61/783,687, filed on Mar. 14, 2013.

(51) Int. Cl.
| | |
|---|---|
| C07C 255/47 | (2006.01) |
| C07C 49/423 | (2006.01) |
| C07C 49/513 | (2006.01) |
| C07D 303/14 | (2006.01) |

(52) U.S. Cl.
CPC .......... *C07D 303/14* (2013.01); *C07C 49/423* (2013.01); *C07C 49/513* (2013.01); *C07C 255/47* (2013.01); *C07C 2603/40* (2017.05); *C07C 2603/42* (2017.05)

(58) Field of Classification Search
USPC .......................... 549/554; 558/429; 568/369
See application file for complete search history.

(56) References Cited

U.S. PATENT DOCUMENTS

| | | |
|---|---|---|
| 3,206,459 A | 9/1965 | Cross et al. |
| 4,071,625 A | 1/1978 | Grunwell et al. |
| 4,179,336 A | 12/1979 | Weber et al. |
| 4,389,345 A | 6/1983 | Lenz |
| 5,925,630 A | 7/1999 | Upasani et al. |
| 7,781,421 B2 | 8/2010 | Covey et al. |
| 2002/0091112 A1 | 7/2002 | Menzenbach et al. |
| 2005/0176976 A1 | 8/2005 | Calogeropoulou et al. |
| 2006/0094696 A1 | 5/2006 | Leese et al. |
| 2009/0048218 A1 | 2/2009 | Kuhnke et al. |
| 2010/0234335 A1 | 9/2010 | Gravanis et al. |

FOREIGN PATENT DOCUMENTS

| | | |
|---|---|---|
| EP | 0104489 A1 | 4/1984 |
| WO | 2012013816 A1 | 2/2012 |
| WO | 2012083090 A2 | 6/2012 |
| WO | 20121162900 A2 | 8/2012 |

OTHER PUBLICATIONS

Ueno et al. (AN 1992:207246 CAPLUS, DN 116:207246; abstract of Analytical Sciences (1992), 8(1), 13-17).*
Scglione et al. (J. Med. Chem. 2008, 51, 1309-1318).*
Jastrzebska et al. (J. Org. Chem. vol. 72. No. 13, pp. 4837-4843, 2007).*
Anderson et al. "Anesthetic Activity of Novel Water-Soluble 2β-Morpholinyl Steroids and Their Modulatory Effects at GABA-A Receptors," J. Med. Chem., 1997, vol. 40, pp. 1668-1681.
Bandyopadhyaya et al., "Neurosteroid analogues. 15. A comparative study of the anesthetic and GABAergic actions of alphaxalone, Δ 16-alphaxalone and their corresponding 17-carbonitrile analogues," Bioorg Med Chem Lett., Nov. 15, 2010, vol. 20, Issue 22, pp. 6680-6684.
Berge et al., J. Pharmaceutical Sciences, 1977, vol. 66, pp. 1-19.
Caspi et al., "Stereochemistry of 19-Hydroxy-19α-methyl steroids," Chemical Communications, 1966, vol. 7, pp. 209-210.
Cerny et al., "Syntheses of 19[O-(carboxymethyl)oxime] haptens of epipregnanolone and pregnanolone," Steroids, 2006, vol. 71(2), pp. 120-128.
Cerny et al., "Synthetic approach to 5alpha-pregnanolone 19-[O-(carboxymethyl) oxime] derivatives," Collection of Czechoslovak Chemical Communications, 2004, vol. 69, No. 9, pp. 1805-1817.
Fajkos et al., "Steroids. XXIII. Synthesis and configuration of the two stereoisomeric 3β-hydroxy-16- acetylandrostanes," Chemicke Listy pro Vedu a Prumysl, 1956, vol. 50, pp. 791-799.
Green et al., "The nonfeminizing enantiomer of 17β-estradiol exerts protective effects in neuronal cultures and a rat model of cerebral ischemia," Endocrinology, 2001, vol. 142, pp. 400-406.
Han et al., "Neurosteroid Analogs. 3. The Synthesis and Electrophysiological Evaluation of Benz[e]indene Congeners of Neuroactive Steroids Having the 5β-Configuration," J. of Med. Chem., 1995, vol. 38, No. 22, pp. 4548-4556.
Hauser et al., "Steroids. CCV. Fragmentations and intramolecular abstractions of tertiary hydrogen atoms by primary oxy radicals with fixed reaction centers," Helv. Chim. Acta, 1964, vol. 47, pp. 1961-1979.
Heard et al., "Steroids. VII. Preparation of androstan-3(β)-ol-7-one from dehydroisoandrosterone," Journal of Biological Chemistry, 1946, vol. 165, pp. 677-685.
Hill et al., "Photochemische Reaktionen. 32 Mitteilung. UV-Bestrahlung von gesattigten and beta,gamma-ungesattigten, homoallylisch konjugierten steroidaldehyden," Helvetica Chimica Acta, 1946, vol. 49, No. 1, pp. 292-311.
Hu et al., "Neurosteroid analogues. Part 5. Enantiomers of neuroactive steroids and benz[e]indenes: total synthesis, electrophysiological effects on GABAA receptor function and anesthetic actions in tadpoles," J. Chem. Soc. Perkin Trans. 1, 1997, pp. 3665-3671.

(Continued)

*Primary Examiner* — Sabiha N Qazi
(74) *Attorney, Agent, or Firm* — Armstrong Teasdale LLP

(57) ABSTRACT

The present disclosure is generally directed to neuroactive substituted cyclopent[a]anthracenes as referenced herein, and pharmaceutically acceptable salts thereof, for use as, for example, an anesthetic, and/or in the treatment of disorders relating to GABA function and activity. The present disclosure is further directed to pharmaceutical compositions comprising such compounds.

6 Claims, 1 Drawing Sheet

(56) References Cited

OTHER PUBLICATIONS

Jastrzebska et al., "Palladium-Catalyzed Potassium Enoxyborate Alkylation of Enantiopure Hajos—Parrish Indenone to Construct Rearranged Steroid Ring Systems," J. Org. Chem., 2007, vol. 72, pp. 4837-4843.
Jiang et al., "Neurosteroid analogues. 9. Conformationally constrained pregnanes: structure-activity studies of 13,24-cyclo-18,21-dinorcholane analogues of the GABA modulatory and anesthetic steroids (3α,5α)- and (3α,5α)-3-hydroxypregnan-20-one" J. Med. Chem., 2003, vol. 46, pp. 5334-5348.
Kaji et al., "Synthesis of 3-epi-6, 7-dideoxyxestobergsterol A," Chem. & Pharm. Bulletin, 2000, vol. 48, No. 10, pp. 1480-1483.
Katona et al., "Neurosteroid analogues. 12. Potent enhancement of GABA-mediated chloride currents at GABAA receptors by ent-androgens," Eur. J. Med. Chem., 2008, vol. 43, pp. 107-113.
Knox et al., "Steroids. CCLXXVIII. Reductions of 19-substituted androst-4-en-3-ones and related compounds," Journal of Organic Chemistry, 1965, vol. 30, No. 7, pp. 2198-2205.
Nilsson et al., "Neurosteroid analogues. 6. The synthesis and GABAA receptor pharmacology of enantiomers of dehydroepiandrosterone sulfate, pregnenolone sulfate, and (3α,5β)-3-hydroxypregnan-20-one sulfate," J. Med. Chem., 1998, vol. 41, pp. 2604-2613.
Qian et al., "Neurosteroid Analogues, 18. Structure-Activity Studies of ent-Steroid Potentiators of γ-Aminobutyric Acid Type A Receptors and Comparison of Their Activities with Those of Alphaxalone and Allopregnanolone," J. of Med. Chem., 2014, vol. 57, No. 1, pp. 171-190.
Qian et al., "The efficient and enantiospecific total synthesis of cyclopenta[b]phenanthrenes structurally related to neurosteroids," Adv. Syn. & Cata., 2010, vol. 352, Nos. 11-12, pp. 2057-2061.
Ruzicka et al., "Steroids and sex hormones. CXXXIX. The relation between constitution and odor of steroids. Methylandrostane and allopregnane derivatives," Helvetica Chimica Acta, 1947, vol. 30, pp. 867-878.
Rychnovsky et al., "Synthesis of ent-cholesterol, the unnatural enantiomer," J. of Org. Chem., 1992, vol. 57, No. 9, pp. 2732-2736.
Santaniello et al., "Reduction of certain steroidal 19-sulfonic esters with metal hydrides," J. of Ster. Biochem., 1976, vol. 7, No. 3, pp. 223-227.
Sarett, L.H., "A new method for the preparation of 17(alpha)-hydroxy-20-ketopregnanes," J. Am. Chem. Soc., 1948, vol. 70, pp. 1454-1458.
Scaglione et al., "Neurosteroid Analogues. 14. Alternative Ring System Scaffolds: GABA Modulatory and Anesthetic Actions of Cyclopenta[b]phenanthrenes and Cyclopenta[b]anthracenes," 2008, J. Med. Chem., vol. 51, pp. 1309-1318.
Shu et al., "Characteristics of concatemeric GABAA receptors containing α4/δ subunits expressed in Xenopus oocytes," British Journal of Pharmacology, 2012, 165, pp. 2228-2243.
Spiegel et al., "Use of Nonaqueous Solvents in Parenteral Products," J. of Pharm. Sciences, 1963, vol. 52, No. 10, pp. 917-927.
Stastna et al., "Stereoselectivity of sodium borohydride reduction of saturated steroidal ketones utilizing conditions of Luche reduction," Steroids, 2010, vol. 75, No. 10, pp. 721-725.
Stastna et al., "Neurosteroid Analogues. 16. A New Explanation for the Lack of Anesthetic Effects in Δ16-Alphaxalone and Identification of a Δ17(20) Analogue with Potent Anesthetic Activity," J. Med. Chem., 2011, vol. 54, No. 11, pp. 3926-3934.
Stastna et al., "The use of symmetry in enantioselective synthesis: Four pairs of chrysene enantiomers prepared from 19-nortestosterone," Org. Biomol. Chem., 2011, vol. 9, pp. 4685-4694.
Ueno et al., "Determination of Two Antiandrogenic Anthrasteroids in Human Serum by Column Switching High-Performance Liquid Chromatography with Electrochemical Detection," Analytical Sciences, 1992, vol. 8, No. 1, pp. 13-17.
Upasani et al., "3α-Hydroxy-3β-(phenylethynyl-5β-pregnan-20-ones: Synthesis and Pharmacological Activity of Neuroactive Steroids with High Affinity for GABA-A Receptors," J. Med. Chem., 1997, vol. 40, pp. 73-84.
Wicha et al., "Transformations of steroidal neopentyl systems. II. Migration of acetate from the 3beta-to the 19-hydroxyl in delta 5 and A/B-trans steroids," Canadian Journal of Chemistry, 1967, vol. 45, No. 7, pp. 707-711.
Wicha et al., "Transformations of steroidal neopentyl systems. VII. Mechanism of the transformation of (19R)-(19)-hydroxy-19-methyl-3-oxo-5alpha-to 3alpha-hydroxy-19-methyl-19-oxo-5alpha-analogs," Journal of Organic Chemistry, 1973, vol. 38 No. 7, pp. 1280-1283.
Wicha et al., "Transformations of steroidal neopentyl systems. V. Synthesis and proof of the configuration of 19amethyl-19 5-alcohols," Journal of the Chemical Society [Section] C: Organic, 1969, vol. 6, pp. 947-951.
Wicha et al., "Transformations of steroidal neopentyl systems. IV. Stereochemistry of products of reaction of methyllithium with steroidal delta5-19-aldehydes," Journal of the Chemical Society [Section] C: Organic, vol. 14, pp. 1740-1746 (1968).
Wu, Pharmaceuticals, 2009, vol. 2, pp. 77-81.
International Search Report and Written Opinion for PCT/US2012/026542, dated Dec. 12, 2012, 14 pages.
International Search Report and Written Opinion for PCT/US2013/076214, dated Jun. 5, 2014, 12 pages.
International Search Report and Written Opinion for PCT/US2014/016405, dated Jul. 16, 2014, 19 pages.
Jiang et al., "Neurosteroid analogues. 9. Conformationally constrained pregnanes: structure-activity studies of 13,24-cyclo-18,21-dinorcholane analogues of the GABA modulatory and anesthetic steroids (3α,5α)- and (3a,5a)-3-hydroxypregnan-20-one" J. Med. Chem., 2003, vol. 46, pp. 5334-5348.

* cited by examiner

Steroid Ring System
(Cyclopenta[a]phenanthrene)

1,6-cyclo-1,10-secosteroid Ring System
(Cyclopenta[a]anthracene)

NEUROACTIVE SUBSTITUTED CYCLOPENT[A]ANTHRACENES AS MODULATORS FOR GABA TYPE-A RECEPTORS

CROSS-REFERENCE TO RELATED APPLICATION

This application is a divisional application and claims priority benefit of U.S. patent application Ser. No. 14/203,678, filed Mar. 11, 2014 and which claims priority benefit of U.S. Provisional Patent Application Ser. No. 61/783,687, filed on Mar. 14, 2013, the entire contents of which are incorporated herein by reference.

GOVERNMENT SUPPORT

This invention was made with Government support under NIH Grant #GM047969, awarded by the National Institute of Health. The Government has certain rights in the invention.

BACKGROUND OF THE DISCLOSURE

The present disclosure is generally directed to novel compounds having utility as an anesthetic and/or in the treatment of disorders relating to GABA function and activity. More specifically, the present disclosure is directed to 1,6-cyclo-1, 10-secosteroids (cyclopent[a]anthracenes) that are neuroactive and suitable for use as an anesthetic, as well as pharmaceutically acceptable salts thereof, and pharmaceutical compositions containing them.

Gamma-aminobutyric acid (GABA) is the major inhibitory neurotransmitter of the central nervous system. GABA activates two types of receptors, the inotropic $GABA_A$ and the metabotropic $GABA_B$ receptor. Activation of the $GABA_B$ receptor by GABA causes hyperpolarization and a resultant inhibition of neurotransmitter release. The $GABA_A$ receptor subtype regulates neuronal excitability and rapid mood changes, such as anxiety, panic, and stress response. $GABA_A$ receptors are chloride ion channels; as a result, activation of the receptor induces increased inward chloride ion flux, resulting in membrane hyperpolarization and neuronal inhibition. Drugs that stimulate $GABA_A$ receptors, such as benzodiazepines and barbiturates, have anticonvulsive effects (by reducing neuronal excitability and raising the seizure threshold), as well as anxiolytic and anesthetic effects.

The effect of certain steroids on $GABA_A$ receptors has been well-established. As a result, researchers continue to pursue the discovery and synthesis of neuroactive steroids that may act as anesthetics and/or that may serve to provide treatment for disorders related to GABA function. For example, it is now widely accepted that the intravenous anesthetic alphaxalone (Compound A, below) causes general anesthesia in humans because it allosterically increases chloride currents mediated by GABA acting at $GABA_A$ receptors in the brain. However, the various structural features that enable this compound to function in the way it does have, to-date, not been fully understood.

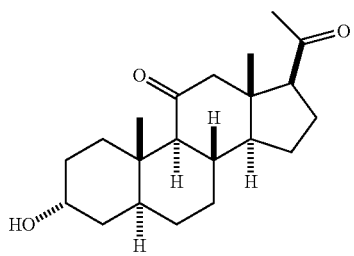

Compound A

In particular, the effect of changing the manner in which the four rings of neurosteroids are connected and the locations of the substituents on alternatively connected rings is not completely understood. The subject of this disclosure is new neurosteroid analogues in which the carbon-carbon bond between positions $C_1$ and $C_{10}$ has been abolished and a new carbon-carbon bond between positions $C_1$ and $C_6$ has been established (see, e.g., FIG. 1A and FIG. 1B). These compounds are named herein as 1,6-cyclo-1,10-secosteroids (cyclopent[a]anthracenes).

In addition to anesthetic properties, neuroactive cyclopent[a]anthracenes may be used to treat disorders related to GABA function. For example, neuroactive cyclopent[a]anthracenes may be used as sedative-hypnotics, exhibiting benzodiazepine-like actions, inducing reduced sleep latency and increased non-REM sleep with only small changes in slow wave and REM sleep. Further, drugs that enhance GABA responses are often used to treat anxiety in humans. Thus, it might be expected that GABA-potentiating cyclopent[a]anthracenes would exhibit anxiolytic effects. Neuroactive cyclopent[a]anthracenes may also be used to treat depression, given that accumulating evidence suggests that patients with major depression have decreased levels of GABAergic neurosteroids and that certain treatments for depression alter levels of these neurosteroids. Although GABA is not typically thought to play a critical role in the biology of depression, there is evidence that low GABAergic activity may predispose one to mood disorders. Finally, inhibition of NMDA receptors and enhancement of $GABA_A$ receptors appear to play important roles in mediating the acute effects of ethanol in the nervous system, while related studies suggest that GABAergic neurosteroids may be involved in some of the pharmacological effects of ethanol and that neuroactive neurosteroids may be useful in treating ethanol withdrawal. Thus, cyclopent[a]anthracenes as analogues of endogenous neurosteroids may be useful for treating these conditions.

In view of the foregoing, it is clear that there are a number of potentially advantageous uses for cyclopent[a]anthracenes. As a result, there is a continuing need for the further synthesis and understanding of new neuroactive cyclopent[a]anthracenes, particularly those having utility as an anesthetic and/or in the treatment of a disorder relating to GABA function and activity.

SUMMARY OF THE DISCLOSURE

In one aspect, the present disclosure is directed to a compound having a structure of Formula (I):

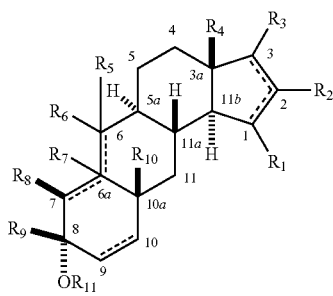

or a pharmaceutically acceptable salt thereof;
wherein:

$R_1$ is H, =O, =CHCN, =CHCO$_2$R$_z$, where R$_z$ is optionally substituted C$_1$-C$_4$ alkyl, optionally substituted C$_2$-C$_4$ alkenyl, or optionally substituted C$_2$-C$_4$ alkynyl, β-CN, β-OH, β-OR$_y$, where R$_y$ is optionally substituted C$_1$-C$_4$ alkyl, optionally substituted C$_2$-C$_4$ alkenyl, or optionally substituted C$_2$-C$_4$ alkynyl, β-NO$_2$, spiroepoxy, or C(O)R$_x$, where R$_x$ is optionally substituted C$_1$-C$_4$ alkyl, optionally substituted C$_2$-C$_4$ alkenyl, or optionally substituted C$_2$-C$_4$ alkynyl;

$R_2$ is H, =O, =CHCN, =CHCO$_2$R$_w$, where R$_w$ is optionally substituted C$_1$-C$_4$ alkyl, optionally substituted C$_2$-C$_4$ alkenyl, or optionally substituted C$_2$-C$_4$ alkynyl, β-CN, β-OH, β-OR$_v$, where R$_v$ is optionally substituted C$_1$-C$_4$ alkyl, optionally substituted C$_2$-C$_4$ alkenyl, or optionally substituted C$_2$-C$_4$ alkynyl, β-NO$_2$, spiroepoxy, or C(O)R$_u$, where R$_u$ is optionally substituted C$_1$-C$_4$ alkyl, optionally substituted C$_2$-C$_4$ alkenyl, or optionally substituted C$_2$-C$_4$ alkynyl;

$R_3$ is H, =O, =CHCN, =CHCO$_2$R$_t$, where R$_t$ is optionally substituted C$_1$-C$_4$ alkyl, optionally substituted C$_2$-C$_4$ alkenyl, or optionally substituted C$_2$-C$_4$ alkynyl, —CN, β-OH, β-OR$_s$, where R$_s$ is optionally substituted C$_1$-C$_4$ alkyl, optionally substituted C$_2$-C$_4$ alkenyl, or optionally substituted C$_2$-C$_4$ alkynyl, β-NO$_2$, spiroepoxy, or C(O)R$_r$, where R$_r$ is optionally substituted C$_1$-C$_4$ alkyl, optionally substituted C$_2$-C$_4$ alkenyl, or optionally substituted C$_2$-C$_4$ alkynyl;

$R_4$ is H, optionally substituted C$_1$-C$_4$ alkyl, optionally substituted C$_2$-C$_4$ alkenyl, or optionally substituted C$_2$-C$_4$ alkynyl;

$R_5$ is H, =O, NH(CH$_3$)$_2$, NH(CH$_2$CH$_3$)$_2$, CH$_2$N(CH$_3$)$_2$, CH$_2$N(CH$_2$CH$_3$)$_2$, CO$_2$R$_q$, where R$_q$ is optionally substituted C$_1$-C$_4$ alkyl, optionally substituted C$_2$-C$_4$ alkenyl, optionally substituted C$_2$-C$_4$ alkynyl, or optionally substituted aryl, CH$_2$OR$_p$, where R$_p$ is optionally substituted C$_1$-C$_4$ alkyl, optionally substituted C$_2$-C$_4$ alkenyl, optionally substituted C$_2$-C$_4$ alkynyl, or optionally substituted aryl, C(O)R$_o$, where R$_o$ is optionally substituted C$_1$-C$_4$ alkyl, optionally substituted C$_2$-C$_4$ alkenyl, optionally substituted C$_2$-C$_4$ alkynyl, or optionally substituted aryl, C(O)NHR$_n$, where R$_n$ is optionally substituted C$_1$-C$_4$ alkyl, optionally substituted C$_2$-C$_4$ alkenyl, optionally substituted C$_2$-C$_4$ alkynyl, or optionally substituted aryl, CH$_2$NHR$_m$, where R$_m$ is optionally substituted C$_1$-C$_4$ alkyl, optionally substituted C$_2$-C$_4$ alkenyl, optionally substituted C$_2$-C$_4$ alkynyl, or optionally substituted aryl, or OR$_l$, where R$_l$ is optionally substituted C$_1$-C$_4$ alkyl, optionally substituted C$_2$-C$_4$ alkenyl, optionally substituted C$_2$-C$_4$ alkynyl, or optionally substituted aryl;

$R_6$ is H, optionally substituted C$_1$-C$_4$ alkyl, optionally substituted C$_2$-C$_4$ alkenyl, or optionally substituted C$_2$-C$_4$ alkynyl;

$R_7$ is H, optionally substituted C$_1$-C$_4$ alkyl, optionally substituted C$_2$-C$_4$ alkenyl, or optionally substituted C$_2$-C$_4$ alkynyl;

$R_8$ is H, optionally substituted morpholinyl, or OR$_k$, where R$_k$ is optionally substituted C$_1$-C$_4$ alkyl, optionally substituted C$_2$-C$_4$ alkenyl, optionally substituted C$_2$-C$_4$ alkynyl, or optionally substituted aryl;

$R_9$ is H, optionally substituted C$_1$-C$_4$ alkyl, optionally substituted C$_2$-C$_4$ alkenyl, optionally substituted C$_2$-C$_4$ alkynyl, or optionally substituted aryl;

$R_{10}$ is H, CH$_2$N(CH$_3$)$_2$, CH$_2$N(CH$_2$CH$_3$)$_2$, CO$_2$R$_j$, where R$_j$ is optionally substituted C$_1$-C$_4$ alkyl, optionally substituted C$_2$-C$_4$ alkenyl, optionally substituted C$_2$-C$_4$ alkynyl, or optionally substituted aryl, CH$_2$OR$_i$, where R$_i$ is optionally substituted C$_1$-C$_4$ alkyl, optionally substituted C$_2$-C$_4$ alkenyl, optionally substituted C$_2$-C$_4$ alkynyl, or optionally substituted aryl, C(O)R$_h$, where R$_h$ is optionally substituted C$_1$-C$_4$ alkyl, optionally substituted C$_2$-C$_4$ alkenyl, optionally substituted C$_2$-C$_4$ alkynyl, or optionally substituted aryl, C(O)NHR$_g$, where R$_g$ is optionally substituted C$_1$-C$_4$ alkyl, optionally substituted C$_2$-C$_4$ alkenyl, optionally substituted C$_2$-C$_4$ alkynyl, or optionally substituted aryl, or CH$_2$NHR$_f$, where R$_f$ is optionally substituted C$_1$-C$_4$ alkyl, optionally substituted C$_2$-C$_4$ alkenyl, optionally substituted C$_2$-C$_4$ alkynyl, or optionally substituted aryl;

$R_{11}$ is H or C(O)R$_e$, where R$_e$ is optionally substituted C$_1$-C$_{20}$ alkyl, optionally substituted C$_2$-C$_{20}$ alkenyl, or optionally substituted C$_2$-C$_{20}$ alkynyl; and,

- - - denotes an optional, additional C—C bond, resulting in either a C=C bond between, C$_1$-C$_2$, C$_2$-C$_3$, C$_6$-C$_{6a}$, C$_{6a}$-C$_7$, or C$_9$-C$_{10}$, with the provisos that when present between: (i) C$_{6a}$-C$_7$, R$_7$ is not present; (ii) C$_6$-C$_{6a}$, R$_7$ is not present and either R$_5$ or R$_6$ is not present, and, when present, R$_5$ is other than =O; (iii) C$_1$-C$_2$, R$_1$ is other than =O, =CHCN or =CHCO$_2$R$_z$, and R$_2$ is other than =O, =CHCN or =CHCO$_2$R$_w$; and, (iv) C$_2$-C$_3$, R$_2$ is other than =O, =CHCN or =CHCO$_2$R$_w$, and R$_3$ is other than =O, =CHCN or =CHCO$_2$R$_t$.

In another aspect, the present disclosure is directed to a compound having a structure of Formula (II):

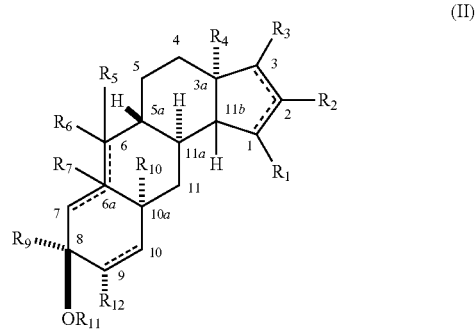

or a pharmaceutically acceptable salt thereof;
wherein:

$R_1$ is H, =O, =CHCN, =CHCO$_2$R$_z$, where R$_z$ is optionally substituted C$_1$-C$_4$ alkyl, optionally substituted C$_2$-C$_4$ alkenyl, or optionally substituted C$_2$-C$_4$ alkynyl, α-CN, α-OH, α-OR$_y$, where R$_y$ is optionally substituted C$_1$-C$_4$ alkyl, optionally substituted C$_2$-C$_4$ alkenyl, or optionally substituted C$_2$-C$_4$ alkynyl, α-NO$_2$, spiroepoxy, or C(O)R$_x$, where $R_x$ is optionally substituted $C_1$-$C_4$ alkyl, optionally substituted $C_2$-$C_4$ alkenyl, or optionally substituted $C_2$-$C_4$ alkynyl;

$R_2$ is H, =O, =CHCN, =CHCO$_2$R$_w$, where R$_w$ is optionally substituted $C_1$-$C_4$ alkyl, optionally substituted $C_2$-$C_4$ alkenyl, or optionally substituted $C_2$-$C_4$ alkynyl, α-CN, α-OH, α-OR$_v$, where R$_v$ is optionally substituted $C_1$-$C_4$ alkyl, optionally substituted $C_2$-$C_4$ alkenyl, or optionally substituted $C_2$-$C_4$ alkynyl, α-NO$_2$, spiroepoxy, or C(O)R$_u$, where R$_u$ is optionally substituted $C_1$-$C_4$ alkyl, optionally substituted $C_2$-$C_4$ alkenyl, or optionally substituted $C_2$-$C_4$ alkynyl;

$R_3$ is H, =O, =CHCN, =CHCO$_2$R$_t$, where R$_t$ is optionally substituted $C_1$-$C_4$ alkyl, optionally substituted $C_2$-$C_4$ alkenyl, or optionally substituted $C_2$-$C_4$ alkynyl, —CN, α-OH, α-OR$_s$, where R$_s$ is optionally substituted $C_1$-$C_4$ alkyl, optionally substituted $C_2$-$C_4$ alkenyl, or optionally substituted $C_2$-$C_4$ alkynyl, α-NO$_2$, spiroepoxy, or C(O)R$_r$, where R$_r$ is optionally substituted $C_1$-$C_4$ alkyl, optionally substituted $C_2$-$C_4$ alkenyl, or optionally substituted $C_2$-$C_4$ alkynyl;

$R_4$ is H, optionally substituted $C_1$-$C_4$ alkyl, optionally substituted $C_2$-$C_4$ alkenyl, or optionally substituted $C_2$-$C_4$ alkynyl;

$R_5$ is H, =O, NH(CH$_3$)$_2$, NH(CH$_2$CH$_3$)$_2$, CH$_2$N(CH$_3$)$_2$, CH$_2$N(CH$_2$CH$_3$)$_2$, CO$_2$R$_q$, where R$_q$ is optionally substituted $C_1$-$C_4$ alkyl, optionally substituted $C_2$-$C_4$ alkenyl, optionally substituted $C_2$-$C_4$ alkynyl, or optionally substituted aryl, CH$_2$OR$_p$, where R$_p$ is optionally substituted $C_1$-$C_4$ alkyl, optionally substituted $C_2$-$C_4$ alkenyl, optionally substituted $C_2$-$C_4$ alkynyl, or optionally substituted aryl, C(O)R$_o$, where R$_o$ is optionally substituted $C_1$-$C_4$ alkyl, optionally substituted $C_2$-$C_4$ alkenyl, optionally substituted $C_2$-$C_4$ alkynyl, or optionally substituted aryl, C(O)NHR$_n$, where R$_n$ is optionally substituted $C_1$-$C_4$ alkyl, optionally substituted $C_2$-$C_4$ alkenyl, optionally substituted $C_2$-$C_4$ alkynyl, or optionally substituted aryl, CH$_2$NHR$_m$, where R$_m$ is optionally substituted $C_1$-$C_4$ alkyl, optionally substituted $C_2$-$C_4$ alkenyl, optionally substituted $C_2$-$C_4$ alkynyl, or optionally substituted aryl, or OR$_l$, where R$_l$ is optionally substituted $C_1$-$C_4$ alkyl, optionally substituted $C_2$-$C_4$ alkenyl, optionally substituted $C_2$-$C_4$ alkynyl, or optionally substituted aryl;

$R_6$ is H, optionally substituted $C_1$-$C_4$ alkyl, optionally substituted $C_2$-$C_4$ alkenyl, or optionally substituted $C_2$-$C_4$ alkynyl;

$R_7$ is H, optionally substituted $C_1$-$C_4$ alkyl, optionally substituted $C_2$-$C_4$ alkenyl, or optionally substituted $C_2$-$C_4$ alkynyl;

$R_9$ is H, optionally substituted $C_1$-$C_4$ alkyl, optionally substituted $C_2$-$C_4$ alkenyl, optionally substituted $C_2$-$C_4$ alkynyl, or optionally substituted aryl;

$R_{10}$ is H, CH$_2$N(CH$_3$)$_2$, CH$_2$N(CH$_2$CH$_3$)$_2$, CO$_2$R$_j$, where R$_j$ is optionally substituted $C_1$-$C_4$ alkyl, optionally substituted $C_2$-$C_4$ alkenyl, optionally substituted $C_2$-$C_4$ alkynyl, or optionally substituted aryl, CH$_2$OR$_i$, where R$_i$ is optionally substituted $C_1$-$C_4$ alkyl, optionally substituted $C_2$-$C_4$ alkenyl, optionally substituted $C_2$-$C_4$ alkynyl, or optionally substituted aryl, C(O)R$_h$, where R$_h$ is optionally substituted $C_1$-$C_4$ alkyl, optionally substituted $C_2$-$C_4$ alkenyl, optionally substituted $C_2$-$C_4$ alkynyl, or optionally substituted aryl, C(O)NHR$_g$, where R$_g$ is optionally substituted $C_1$-$C_4$ alkyl, optionally substituted $C_2$-$C_4$ alkenyl, optionally substituted $C_2$-$C_4$ alkynyl, or optionally substituted aryl, or CH$_2$NHR$_f$, where R$_f$ is optionally substituted $C_1$-$C_4$ alkyl, optionally substituted $C_2$-$C_4$ alkenyl, optionally substituted $C_2$-$C_4$ alkynyl, or optionally substituted aryl;

$R_{11}$ is H or C(O)R$_e$, where R$_e$ is optionally substituted $C_1$-$C_{20}$ alkyl, optionally substituted $C_2$-$C_{20}$ alkenyl, or optionally substituted $C_2$-$C_{20}$ alkynyl;

$R_{12}$ is H, optionally substituted morpholinyl, or OR$_k$, where R$_k$ is optionally substituted $C_1$-$C_4$ alkyl, optionally substituted $C_2$-$C_4$ alkenyl, optionally substituted $C_2$-$C_4$ alkynyl, or optionally substituted aryl; and,

- - - denotes an optional, additional C—C bond, resulting in either a C=C bond between, $C_1$-$C_2$, $C_2$-$C_3$, $C_6$-$C_{6a}$, $C_{6a}$-$C_7$, or $C_9$-$C_{10}$, with the provisos that when present between: (i) $C_{6a}$-$C_7$, $R_7$ is not present; (ii) $C_6$-$C_{6a}$, $R_7$ is not present and either $R_5$ or $R_6$ is not present, and, when present, $R_5$ is other than =O; (iii) $C_1$-$C_2$, $R_1$ is other than =O, =CHCN or =CHCO$_2$R$_z$, and $R_2$ is other than =O, =CHCN or =CHCO$_2$R$_w$; and, (iv) $C_2$-$C_3$, $R_2$ is other than =O, =CHCN or =CHCO$_2$R$_w$, and $R_3$ is other than =O, =CHCN or =CHCO$_2$R$_t$.

The present disclosure is still further directed to a pharmaceutical composition comprising a therapeutically effective amount of one or more of the above-noted cyclopent[a]anthracenes or pharmaceutically acceptable salts thereof, and optionally a pharmaceutically acceptable carrier. The present disclosure also provides kits comprising cyclopent[a]anthracenes, salts thereof, and/or pharmaceutical compositions thereof.

The present disclosure further provides methods of inducing anesthesia in a subject in need thereof, the method comprising administering to the subject a therapeutically effective amount of one or more of the above-noted cyclopent[a]anthracenes, or pharmaceutically acceptable salts thereof, or a pharmaceutical composition thereof.

The present disclosure further provides methods of treating disorders related to GABA function in a subject in need thereof, the method comprising administering to the subject a therapeutically effective amount of one or more of the above-noted cyclopent[a]anthracenes, or pharmaceutically acceptable salts thereof, or a pharmaceutical composition thereof. In certain embodiments, the disorder is selected from the group consisting of insomnia, mood disorders, convulsive disorders, Fragile X syndrome, anxiety, or symptoms of ethanol withdrawal.

DETAILED DESCRIPTION OF CERTAIN EMBODIMENTS

Figure 1A:
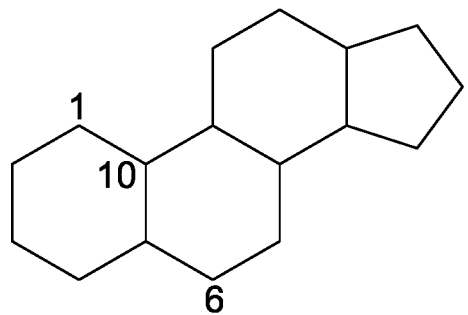
FIG. 1A is an exemplary embodiment of a cyclopent[a]phenanthrene.
Figure 1B:
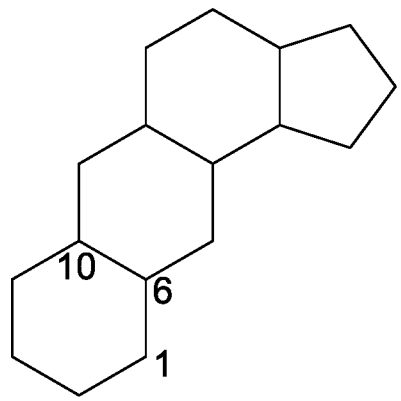
FIG. 1B is an exemplary embodiment of a cyclopent[a]anthracene.

In accordance with the present disclosure, it has been discovered that compounds having certain substituted cyclopent[a]anthracene structures are neuroactive and are also suitable for use as anesthetics and in the treatment of disorders associated with GABA function, as well as pharmaceutically acceptable salts thereof. The compounds may be used, for example, as an effective continuous infusion sedative for non-surgical procedures (e.g., colonoscopy). The compounds also offer advantages over anesthetics known in the art, such as a lower likelihood for bacterial contamination, as well as an improved relationship with solubilizing agents.

1A. Cyclopent[a]anthracene Structure

Generally speaking, in one embodiment, the cyclopent[a]anthracene of the present disclosure has a tetracyclic, fused ring structure (an embodiment of which is illustrated and discussed in greater detail below), wherein the $C_8$-position of the A ring has a hydroxyl or an ester substituent in the alpha configuration and the $C_3$ position has a substituent attached thereto selected from the group consisting of H, =O, =CHCN, =CHCO$_2$R$_t$, where R$_t$ is optionally substituted $C_1$-$C_4$ alkyl, optionally substituted $C_2$-$C_4$ alkenyl, or optionally substituted $C_2$-$C_4$ alkynyl, —CN, β-OH, β-OR$_s$, where R$_s$ is optionally substituted $C_1$-$C_4$ alkyl, optionally substituted $C_2$-$C_4$ alkenyl, or optionally substituted $C_2$-$C_4$ alkynyl, β-NO$_2$, spiroepoxy, and C(O)R$_r$, where R$_r$ is optionally substituted $C_1$-$C_4$ alkyl, optionally substituted $C_2$-$C_4$ alkenyl, or optionally substituted $C_2$-$C_4$ alkynyl.

More particularly, however, the present disclosure is directed, in certain embodiments, to a cyclopent[a]anthracene having the structure of Formula (I):

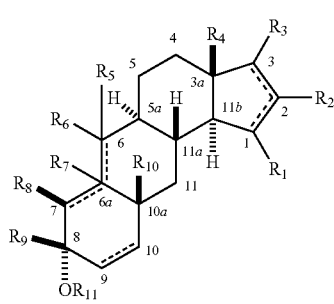

(I)

or a pharmaceutically acceptable salt thereof;
wherein:
$R_1$ is H, =O, =CHCN, =CHCO$_2$R$_z$, where R$_z$ is optionally substituted $C_1$-$C_4$ alkyl, optionally substituted $C_2$-$C_4$ alkenyl, or optionally substituted $C_2$-$C_4$ alkynyl, β-CN, β-OH, β-OR$_y$, where R$_y$ is optionally substituted $C_1$-$C_4$ alkyl, optionally substituted $C_2$-$C_4$ alkenyl, or optionally substituted $C_2$-$C_4$ alkynyl, β-NO$_2$, spiroepoxy, or C(O)R$_x$, where R$_x$ is optionally substituted $C_1$-$C_4$ alkyl, optionally substituted $C_2$-$C_4$ alkenyl, or optionally substituted $C_2$-$C_4$ alkynyl;

$R_2$ is H, =O, =CHCN, =CHCO$_2$R$_w$, where R$_w$ is optionally substituted $C_1$-$C_4$ alkyl, optionally substituted $C_2$-$C_4$ alkenyl, or optionally substituted $C_2$-$C_4$ alkynyl, β-CN, β-OH, β-OR$_v$, where R$_v$ is optionally substituted $C_1$-$C_4$ alkyl, optionally substituted $C_2$-$C_4$ alkenyl, or optionally substituted $C_2$-$C_4$ alkynyl, β-NO$_2$, spiroepoxy, or C(O)R$_u$, where R$_u$ is optionally substituted $C_1$-$C_4$ alkyl, optionally substituted $C_2$-$C_4$ alkenyl, or optionally substituted $C_2$-$C_4$ alkynyl;

$R_3$ is H, =O, =CHCN, =CHCO$_2$R$_t$, where R$_t$ is optionally substituted $C_1$-$C_4$ alkyl, optionally substituted $C_2$-$C_4$ alkenyl, or optionally substituted $C_2$-$C_4$ alkynyl, —CN, β-OH, β-OR$_s$, where R$_s$ is optionally substituted $C_1$-$C_4$ alkyl, optionally substituted $C_2$-$C_4$ alkenyl, or optionally substituted $C_2$-$C_4$ alkynyl, β-NO$_2$, spiroepoxy, or C(O)R$_r$, where R$_r$ is optionally substituted $C_1$-$C_4$ alkyl, optionally substituted $C_2$-$C_4$ alkenyl, or optionally substituted $C_2$-$C_4$ alkynyl;

$R_4$ is H, optionally substituted $C_1$-$C_4$ alkyl, optionally substituted $C_2$-$C_4$ alkenyl, or optionally substituted $C_2$-$C_4$ alkynyl;

$R_5$ is H, =O, NH(CH$_3$)$_2$, NH(CH$_2$CH$_3$)$_2$, CH$_2$N(CH$_3$)$_2$, CH$_2$N(CH$_2$CH$_3$)$_2$, CO$_2$R$_q$, where R$_q$ is optionally substituted $C_1$-$C_4$ alkyl, optionally substituted $C_2$-$C_4$ alkenyl, optionally substituted $C_2$-$C_4$ alkynyl, or optionally substituted aryl, CH$_2$OR$_p$, where R$_p$ is optionally substituted $C_1$-$C_4$ alkyl, optionally substituted $C_2$-$C_4$ alkenyl, optionally substituted $C_2$-$C_4$ alkynyl, or optionally substituted aryl, C(O)R$_o$, where R$_o$ is optionally substituted $C_1$-$C_4$ alkyl, optionally substituted $C_2$-$C_4$ alkenyl, optionally substituted $C_2$-$C_4$ alkynyl, or optionally substituted aryl, C(O)NHR$_n$, where R$_n$ is optionally substituted $C_1$-$C_4$ alkyl, optionally substituted $C_2$-$C_4$ alkenyl, optionally substituted $C_2$-$C_4$ alkynyl, or optionally substituted aryl, CH$_2$NHR$_m$, where R$_m$ is optionally substituted $C_1$-$C_4$ alkyl, optionally substituted $C_2$-$C_4$ alkenyl, optionally substituted $C_2$-$C_4$ alkynyl, or optionally substituted aryl, or OR$_l$, where R$_l$ is optionally substituted $C_1$-$C_4$ alkyl, optionally substituted $C_2$-$C_4$ alkenyl, optionally substituted $C_2$-$C_4$ alkynyl, or optionally substituted aryl;

$R_6$ is H, optionally substituted $C_1$-$C_4$ alkyl, optionally substituted $C_2$-$C_4$ alkenyl, or optionally substituted $C_2$-$C_4$ alkynyl;

$R_7$ is H, optionally substituted $C_1$-$C_4$ alkyl, optionally substituted $C_2$-$C_4$ alkenyl, or optionally substituted $C_2$-$C_4$ alkynyl;

$R_8$ is H, optionally substituted morpholinyl, or OR$_k$, where R$_k$ is optionally substituted $C_1$-$C_4$ alkyl, optionally substituted $C_2$-$C_4$ alkenyl, optionally substituted $C_2$-$C_4$ alkynyl, or optionally substituted aryl;

$R_9$ is H, optionally substituted $C_1$-$C_4$ alkyl, optionally substituted $C_2$-$C_4$ alkenyl, or optionally substituted $C_2$-$C_4$ alkynyl, or optionally substituted aryl;

$R_{10}$ is H, CH$_2$N(CH$_3$)$_2$, CH$_2$N(CH$_2$CH$_3$)$_2$, CO$_2$R$_j$, where R$_j$ is optionally substituted $C_1$-$C_4$ alkyl, optionally substituted $C_2$-$C_4$ alkenyl, optionally substituted $C_2$-$C_4$ alkynyl, or optionally substituted aryl, CH$_2$OR$_i$, where R$_i$ is optionally substituted $C_1$-$C_4$ alkyl, optionally substituted $C_2$-$C_4$ alkenyl, optionally substituted $C_2$-$C_4$ alkynyl, or optionally substituted aryl, C(O)R$_h$, where R$_h$ is optionally substituted $C_1$-$C_4$ alkyl, optionally substituted $C_2$-$C_4$ alkenyl, optionally substituted $C_2$-$C_4$ alkynyl, or optionally substituted aryl, C(O)NHR$_g$, where R$_g$ is optionally substituted $C_1$-$C_4$ alkyl, optionally substituted $C_2$-$C_4$ alkenyl, optionally substituted $C_2$-$C_4$ alkynyl, or optionally substituted aryl, or CH$_2$NHR$_f$, where R$_f$ is optionally substituted $C_1$-$C_4$ alkyl, optionally substituted $C_2$-$C_4$ alkenyl, optionally substituted $C_2$-$C_4$ alkynyl, or optionally substituted aryl;

$R_{11}$ is H or C(O)R$_e$, where R$_e$ is optionally substituted $C_1$-$C_{20}$ alkyl, optionally substituted $C_2$-$C_{20}$ alkenyl, or optionally substituted $C_2$-$C_{20}$ alkynyl; and,

- - - denotes an optional, additional C—C bond, resulting in either a C=C bond between, $C_1$-$C_2$, $C_2$-$C_3$, $C_6$-$C_{6a}$, $C_{6a}$-$C_7$, or $C_9$-$C_{10}$, with the provisos that when present between: (i) $C_{6a}$-$C_7$, $R_7$ is not present; (ii) $C_6$-$C_{6a}$, $R_7$ is not present and either $R_5$ or $R_6$ is not present, and, when present, $R_5$ is other than =O; (iii) $C_1$-$C_2$, $R_1$ is other than =O, =CHCN or =CHCO$_2$R$_z$, and $R_2$ is other than =O, =CHCN or =CHCO$_2$R$_w$; and, (iv) $C_2$-$C_3$, $R_2$ is other than =O, =CHCN or =CHCO$_2$R$_w$, and $R_3$ is other than =O, =CHCN or =CHCO$_2$R$_t$.

As generally defined above, $R_1$ is H, =O, =CHCN, =CHCO$_2$R$_z$, where R$_z$ is optionally substituted $C_1$-$C_4$ alkyl, optionally substituted $C_2$-$C_4$ alkenyl, or optionally substituted $C_2$-$C_4$ alkynyl, β-CN, β-OH, β-OR$_y$, where R$_y$ is optionally substituted $C_1$-$C_4$ alkyl, optionally substituted $C_2$-$C_4$ alkenyl, or optionally substituted $C_2$-$C_4$ alkynyl, β-NO$_2$, spiroepoxy, or C(O)R$_x$, where R$_x$ is optionally substituted $C_1$-$C_4$ alkyl, optionally substituted $C_2$-$C_4$ alkenyl, or optionally substituted $C_2$-$C_4$ alkynyl. In a preferred embodiment, $R_1$ is H.

As generally defined above, $R_2$ is H, =O, =CHCN, =CHCO$_2$R$_w$, where R$_w$ is optionally substituted $C_1$-$C_4$ alkyl, optionally substituted $C_2$-$C_4$ alkenyl, or optionally substituted $C_2$-$C_4$ alkynyl, β-CN, β-OH, β-OR$_v$, where R$_v$ is optionally substituted $C_1$-$C_4$ alkyl, optionally substituted $C_2$-$C_4$ alkenyl, or optionally substituted $C_2$-$C_4$ alkynyl, β-NO$_2$, spiroepoxy, or C(O)R$_u$, where R$_u$ is optionally substituted $C_1$-$C_4$ alkyl, optionally substituted $C_2$-$C_4$ alkenyl, or optionally substituted $C_2$-$C_4$ alkynyl. In a preferred embodiment, $R_2$ is H.

As generally defined above, $R_3$ is H, =O, =CHCN, =CHCO$_2$R$_t$, where R$_t$ is optionally substituted $C_1$-$C_4$ alkyl, optionally substituted $C_2$-$C_4$ alkenyl, or optionally substituted $C_2$-$C_4$ alkynyl, —CN, β-OH, β-OR$_s$, where R$_s$ is optionally substituted $C_1$-$C_4$ alkyl, optionally substituted $C_2$-$C_4$ alkenyl, or optionally substituted $C_2$-$C_4$ alkynyl, β-NO$_2$, spiroepoxy, or C(O)R$_r$, where R$_r$ is optionally substituted $C_1$-$C_4$ alkyl, optionally substituted $C_2$-$C_4$ alkenyl, or optionally substituted $C_2$-$C_4$ alkynyl. In certain embodiments, $R_3$ is =O. In other certain embodiments, $R_3$ is spiroepoxy. In other certain embodiments, $R_3$ is β-CN. In other certain embodiments, when a double bond is present between $C_2$-$C_3$, $R_3$ is —CN.

As generally defined above, $R_4$ is H, optionally substituted $C_1$-$C_4$ alkyl, optionally substituted $C_2$-$C_4$ alkenyl, or optionally substituted $C_2$-$C_4$ alkynyl. In a preferred embodiment, $R_4$ is methyl. $R_4$ is in the beta configuration.

As generally defined above, $R_5$ is H, =O, NH(CH$_3$)$_2$, NH(CH$_2$CH$_3$)$_2$, CH$_2$N(CH$_3$)$_2$, CH$_2$N(CH$_2$CH$_3$)$_2$, CO$_2$R$_q$, where R$_q$ is optionally substituted $C_1$-$C_4$ alkyl, optionally substituted $C_2$-$C_4$ alkenyl, optionally substituted $C_2$-$C_4$ alkynyl, or optionally substituted aryl, CH$_2$OR$_p$, where R$_p$ is optionally substituted $C_1$-$C_4$ alkyl, optionally substituted $C_2$-$C_4$ alkenyl, optionally substituted $C_2$-$C_4$ alkynyl, or optionally substituted aryl, C(O)R$_o$, where R$_o$ is optionally substituted $C_1$-$C_4$ alkyl, optionally substituted $C_2$-$C_4$ alkenyl, optionally substituted $C_2$-$C_4$ alkynyl, or optionally substituted aryl, C(O)NHR$_n$, where R$_n$ is optionally substituted $C_1$-$C_4$ alkyl, optionally substituted $C_2$-$C_4$ alkenyl, optionally substituted $C_2$-$C_4$ alkynyl, or optionally substituted aryl, CH$_2$NHR$_m$, where R$_m$ is optionally substituted $C_1$-$C_4$ alkyl, optionally substituted $C_2$-$C_4$ alkenyl, optionally substituted $C_2$-$C_4$ alkynyl, or optionally substituted aryl, or OR$_l$, where R$_l$ is optionally substituted $C_1$-$C_4$ alkyl, optionally substituted $C_2$-$C_4$ alkenyl, optionally substituted $C_2$-$C_4$ alkynyl, or optionally substituted aryl. In certain embodiments, the optionally substituted aryl is optionally substituted phenyl or naphthyl. In a preferred embodiment, $R_5$ is H.

As generally defined above, $R_6$ is H, optionally substituted $C_1$-$C_4$ alkyl, optionally substituted $C_2$-$C_4$ alkenyl, or optionally substituted $C_2$-$C_4$ alkynyl. In a preferred embodiment, $R_6$ is H.

As generally defined above, $R_7$ is H, optionally substituted $C_1$-$C_4$ alkyl, optionally substituted $C_2$-$C_4$ alkenyl, or optionally substituted $C_2$-$C_4$ alkynyl. In a preferred embodiment, $R_7$ is H. In a preferred embodiment, $R_7$ is in the alpha configuration.

As generally defined above, $R_8$ is H, optionally substituted morpholinyl, or OR$_k$, where R$_k$ is optionally substituted $C_1$-$C_4$ alkyl, optionally substituted $C_2$-$C_4$ alkenyl, optionally substituted $C_2$-$C_4$ alkynyl, or optionally substituted aryl. In certain embodiments, the optionally substituted aryl is optionally substituted phenyl or naphthyl. In a preferred embodiment, $R_8$ is H. $R_8$ is in the beta configuration.

As generally defined above, $R_9$ is H, optionally substituted $C_1$-$C_4$ alkyl, optionally substituted $C_2$-$C_4$ alkenyl, optionally substituted $C_2$-$C_4$ alkynyl, or optionally substituted aryl. In other certain embodiments, the optionally substituted alkyl is alkyl aryl, such as alkyl benzyl. In a preferred embodiment, $R_9$ is H. $R_9$ is in the beta configuration.

As generally defined above, $R_{10}$ is H, CH$_2$N(CH$_3$)$_2$, CH$_2$N(CH$_2$CH$_3$)$_2$, CO$_2$R$_j$, where R$_j$ is optionally substituted $C_1$-$C_4$ alkyl, optionally substituted $C_2$-$C_4$ alkenyl, optionally substituted $C_2$-$C_4$ alkynyl, or optionally substituted aryl, CH$_2$OR$_i$, where R$_i$ is optionally substituted $C_1$-$C_4$ alkyl, optionally substituted $C_2$-$C_4$ alkenyl, optionally substituted $C_2$-$C_4$ alkynyl, or optionally substituted aryl, C(O)R$_h$, where R$_h$ is optionally substituted $C_1$-$C_4$ alkyl, optionally substituted $C_2$-$C_4$ alkenyl, optionally substituted $C_2$-$C_4$ alkynyl, or optionally substituted aryl, C(O)NHR$_g$, where R$_g$ is optionally substituted $C_1$-$C_4$ alkyl, optionally substituted $C_2$-$C_4$ alkenyl, optionally substituted $C_2$-$C_4$ alkynyl, or optionally substituted aryl, or CH$_2$NHR$_f$, where R$_f$ is optionally substituted $C_1$-$C_4$ alkyl, optionally substituted $C_2$-$C_4$ alkenyl, optionally substituted $C_2$-$C_4$ alkynyl, or optionally substituted aryl. In a preferred embodiment, $R_{10}$ is H. $R_{10}$ is in the beta configuration.

As generally defined above, $R_{11}$ is H or C(O)R$_e$, where R$_e$ is optionally substituted $C_1$-$C_{20}$ alkyl, optionally substituted $C_2$-$C_{20}$ alkenyl, or optionally substituted $C_2$-$C_{20}$ alkynyl. In one embodiment, R$_e$ is optionally substituted $C_1$-$C_{15}$ alkyl, preferably optionally substituted $C_1$-$C_{10}$ alkyl, more preferably optionally substituted $C_1$-$C_4$ alkyl. In another embodiment, R$_e$ is optionally substituted $C_1$-$C_{15}$ alkenyl, preferably optionally substituted $C_1$-$C_{10}$ alkenyl, more preferably optionally substituted $C_1$-$C_4$ alkenyl. In yet another embodiment, R$_e$ is optionally substituted $C_1$-$C_{15}$ alkynyl, preferably optionally substituted $C_1$-$C_{10}$ alkynyl, more preferably optionally substituted $C_1$-$C_4$ alkynyl. In a preferred embodiment, $R_{11}$ is H.

As generally defined above, - - - denotes an optional, additional C—C bond, resulting in either a C=C bond between, $C_1$-$C_2$, $C_2$-$C_3$, $C_6$-$C_{6a}$, $C_{6a}$-$C_7$, or $C_9$-$C_{10}$, with the provisos that when present between: (i) $C_{6a}$-$C_7$, $R_7$ is not present; (ii) $C_6$-$C_{6a}$, $R_7$ is not present and either $R_5$ or $R_6$ is not present, and, when present, $R_5$ is other than =O; (iii) $C_1$-$C_2$, $R_1$ is other than =O, =CHCN or =CHCO$_2$R$_z$, and $R_2$ is other than =O, =CHCN or =CHCO$_2$R$_w$; and, (iv) $C_2$-$C_3$, $R_2$ is other than =O, =CHCN or =CHCO$_2$R$_w$, and $R_3$ is other than =O, =CHCN or =CHCO$_2$R$_t$.

In one embodiment, a double bond is present between $C_9$-$C_{10}$. In another embodiment, a double bond is present between $C_{6a}$-$C_7$. In yet another embodiment, a double bond is present between $C_6$-$C_{6a}$. When a double bond is present between either $C_{6a}$-$C_7$ or $C_6$-$C_{6a}$, $R_7$ is not present. Further, when a double bond is present between $C_6$-$C_{6a}$, either $R_5$ or $R_6$ is not present, and, when present, $R_5$ is other than =O.

In other certain embodiments, a double bond is present between $C_1$-$C_2$. When a double bond is present between $C_1$-$C_2$, $R_1$ is other than =O, =CHCN or =CHCO$_2$R$_z$, and $R_2$ is other than =O, =CHCN or =CHCO$_2$R$_w$. In other certain embodiments, a double bond is present between $C_2$-$C_3$. When a double bond is present between $C_2$-$C_3$, $R_2$ is other than =O, =CHCN or =CHCO$_2$R$_w$, and $R_3$ is other than =O, =CHCN or =CHCO$_2$R$_t$. In one embodiment, when a double bond is present between $C_2$-$C_3$, $R_3$ is —CN.

It is to be noted that the present disclosure contemplates and is intended to encompass all of the various combinations and permutations (i.e., combinations of substituent options, locations and stereochemical configurations) possible here.

For example, in various embodiments, compounds of the present disclosure have the formula of (I-a):

11

(I-a)

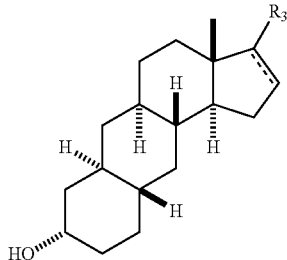

wherein:

$R_3$ is =O, =CHCN, =CHCO$_2$R$_t$, where R$_t$ is optionally substituted C$_1$-C$_4$ alkyl, optionally substituted C$_2$-C$_4$ alkenyl, or optionally substituted C$_2$-C$_4$ alkynyl, —CN, β-OH, β-OR$_s$, where R$_s$ is optionally substituted C$_1$-C$_4$ alkyl, optionally substituted C$_2$-C$_4$ alkenyl, or optionally substituted C$_2$-C$_4$ alkynyl, β-NO$_2$, spiroepoxy, or C(O)R$_r$, where R$_r$ is optionally substituted C$_1$-C$_4$ alkyl, optionally substituted C$_2$-C$_4$ alkenyl, or optionally substituted C$_2$-C$_4$ alkynyl; and,

- - - denotes an optional C—C bond, resulting in a C=C bond between C$_2$-C$_3$ with the proviso that when present, R$_3$ is other than =O, =CHCN or =CHCO$_2$R$_t$.

As generally defined above in Formula (I-a), R$_3$ is =O, =CHCN, =CHCO$_2$R$_t$, where R$_t$ is optionally substituted C$_1$-C$_4$ alkyl, optionally substituted C$_2$-C$_4$ alkenyl, or optionally substituted C$_2$-C$_4$ alkynyl, —CN, β-OH, β-OR$_s$, where R$_s$ is optionally substituted C$_1$-C$_4$ alkyl, optionally substituted C$_2$-C$_4$ alkenyl, or optionally substituted C$_2$-C$_4$ alkynyl, β-NO$_2$, spiroepoxy, or C(O)R$_r$, where R$_r$ is optionally substituted C$_1$-C$_4$ alkyl, optionally substituted C$_2$-C$_4$ alkenyl, or optionally substituted C$_2$-C$_4$ alkynyl. In certain embodiments, R$_3$ is =O. In other certain embodiments, R$_3$ is spiroepoxy. In other certain embodiments, R$_3$ is β-CN.

As generally defined above in Formula (I-a), - - - denotes an optional C—C bond, resulting in a C=C bond between C$_2$-C$_3$. In one embodiment a double bond is present between C$_2$-C$_3$. When a double bond is present between C$_2$-C$_3$ in Formula (I-a), R$_3$ is —CN.

Accordingly, as noted, the cyclopent[a]anthracenes of Formulas (I) and (I-a) may encompass a number of various structures in accordance with the present disclosure, including all of the various combinations and permutations (i.e., combinations of substituent options, locations and stereochemical configurations) possible here.

Exemplary compounds of Formula (I) include, but are not limited to:

(MQ-74)

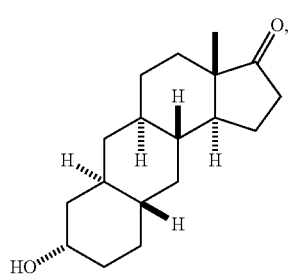

12

-continued (MQ-75)

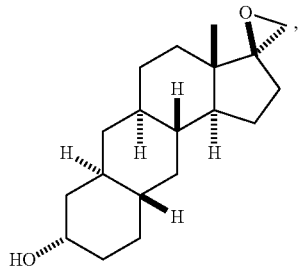

(MQ-76)

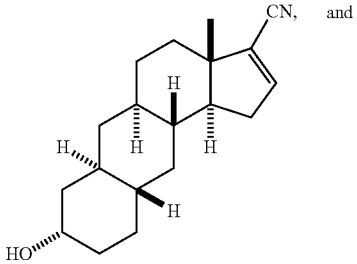

(MQ-77)

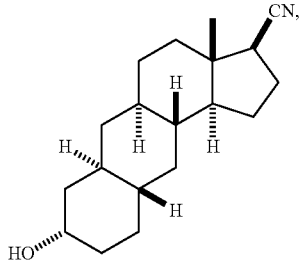

and pharmaceutically acceptable salts thereof.

In this regard it is to be noted that the structures provided above are of various exemplary embodiments. As such, they should not be viewed in a limiting sense.

1B. Cyclopent[a]anthracene Structure

Generally speaking, in another embodiment, the cyclopent[a]anthracene of the present disclosure has a tetracyclic, fused ring structure (an embodiment of which is illustrated and discussed in greater detail below), wherein the C$_8$-position of the A ring has a hydroxyl or an ester substituent in the beta configuration, the C$_3$ position has a substituent attached thereto selected from the group consisting of H, =O, =CHCN, =CHCO$_2$R$_t$, where R$_t$ is optionally substituted C$_1$-C$_4$ alkyl, optionally substituted C$_2$-C$_4$ alkenyl, or optionally substituted C$_2$-C$_4$ alkynyl, —CN, α-OH, α-OR$_s$, where R$_s$ is optionally substituted C$_1$-C$_4$ alkyl, optionally substituted C$_2$-C$_4$ alkenyl, or optionally substituted C$_2$-C$_4$ alkynyl, α-NO$_2$, spiroepoxy, and C(O)R$_r$, where R$_r$ is optionally substituted C$_1$-C$_4$ alkyl, optionally substituted C$_2$-C$_4$ alkenyl, or optionally substituted C$_2$-C$_4$ alkynyl; and the C$_2$ position has a substituent attached thereto selected from the group consisting of H, =O, =CHCN, =CHCO$_2$R$_w$, where R$_w$ is optionally substituted C$_1$-C$_4$ alkyl, optionally substituted C$_2$-C$_4$ alkenyl, or optionally substituted C$_2$-C$_4$ alkynyl, α-CN, α-OH, α-OR$_v$, where R$_v$ is optionally substituted C$_1$-C$_4$ alkyl, optionally substituted C$_2$-C$_4$ alkenyl, or optionally substituted C$_2$-C$_4$ alkynyl, α-NO$_2$, spiroepoxy, and C(O)R$_u$, where R$_u$ is optionally substituted C$_1$-C$_4$ alkyl, optionally substituted C$_2$-C$_4$ alkenyl, or optionally substituted C$_2$-C$_4$ alkynyl.

More particularly, however, the present disclosure is directed, in certain embodiments, to a cyclopent[a]anthracene having the structure of Formula (II):

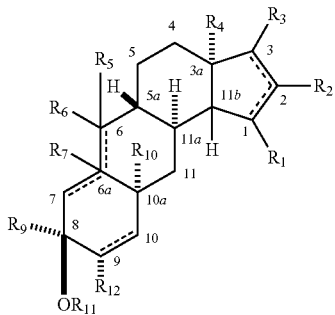

(II)

or a pharmaceutically acceptable salt thereof;
wherein:

$R_1$ is H, =O, =CHCN, =CHCO$_2$R$_z$, where R$_z$ is optionally substituted $C_1$-$C_4$ alkyl, optionally substituted $C_2$-$C_4$ alkenyl, or optionally substituted $C_2$-$C_4$ alkynyl, α-CN, α-OH, α-OR$_y$, where R$_y$ is optionally substituted $C_1$-$C_4$ alkyl, optionally substituted $C_2$-$C_4$ alkenyl, or optionally substituted $C_2$-$C_4$ alkynyl, α-NO$_2$, spiroepoxy, or C(O)R$_x$, where R$_x$ is optionally substituted $C_1$-$C_4$ alkyl, optionally substituted $C_2$-$C_4$ alkenyl, or optionally substituted $C_2$-$C_4$ alkynyl;

$R_2$ is H, =O, =CHCN, =CHCO$_2$R$_w$, where R$_w$ is optionally substituted $C_1$-$C_4$ alkyl, optionally substituted $C_2$-$C_4$ alkenyl, or optionally substituted $C_2$-$C_4$ alkynyl, α-CN, α-OH, α-OR$_v$, where R$_v$ is optionally substituted $C_1$-$C_4$ alkyl, optionally substituted $C_2$-$C_4$ alkenyl, or optionally substituted $C_2$-$C_4$ alkynyl, α-NO$_2$, spiroepoxy, or C(O)R$_u$, where R$_u$ is optionally substituted $C_1$-$C_4$ alkyl, optionally substituted $C_2$-$C_4$ alkenyl, or optionally substituted $C_2$-$C_4$ alkynyl;

$R_3$ is H, =O, =CHCN, =CHCO$_2$R$_t$, where R$_t$ is optionally substituted $C_1$-$C_4$ alkyl, optionally substituted $C_2$-$C_4$ alkenyl, or optionally substituted $C_2$-$C_4$ alkynyl, —CN, α-OH, α-OR$_s$, where R$_s$ is optionally substituted $C_1$-$C_4$ alkyl, optionally substituted $C_2$-$C_4$ alkenyl, or optionally substituted $C_2$-$C_4$ alkynyl, α-NO$_2$, spiroepoxy, or C(O)R$_r$, where R$_r$ is optionally substituted $C_1$-$C_4$ alkyl, optionally substituted $C_2$-$C_4$ alkenyl, or optionally substituted $C_2$-$C_4$ alkynyl;

$R_4$ is H, optionally substituted $C_1$-$C_4$ alkyl, optionally substituted $C_2$-$C_4$ alkenyl, or optionally substituted $C_2$-$C_4$ alkynyl;

$R_5$ is H, =O, NH(CH$_3$)$_2$, NH(CH$_2$CH$_3$)$_2$, CH$_2$N(CH$_3$)$_2$, CH$_2$N(CH$_2$CH$_3$)$_2$, CO$_2$R$_q$, where R$_q$ is optionally substituted $C_1$-$C_4$ alkyl, optionally substituted $C_2$-$C_4$ alkenyl, optionally substituted $C_2$-$C_4$ alkynyl, or optionally substituted aryl, CH$_2$OR$_p$, where R$_p$ is optionally substituted $C_1$-$C_4$ alkyl, optionally substituted $C_2$-$C_4$ alkenyl, optionally substituted $C_2$-$C_4$ alkynyl, or optionally substituted aryl, C(O)R$_o$, where R$_o$ is optionally substituted $C_1$-$C_4$ alkyl, optionally substituted $C_2$-$C_4$ alkenyl, optionally substituted $C_2$-$C_4$ alkynyl, or optionally substituted aryl, C(O)NHR$_n$, where R$_n$ is optionally substituted $C_1$-$C_4$ alkyl, optionally substituted $C_2$-$C_4$ alkenyl, optionally substituted $C_2$-$C_4$ alkynyl, or optionally substituted aryl, CH$_2$NHR$_m$, where R$_m$ is optionally substituted $C_1$-$C_4$ alkyl, optionally substituted $C_2$-$C_4$ alkenyl, optionally substituted $C_2$-$C_4$ alkynyl, or optionally substituted aryl, or OR$_l$, where R$_l$ is optionally substituted $C_1$-$C_4$ alkyl, optionally substituted $C_2$-$C_4$ alkenyl, optionally substituted $C_2$-$C_4$ alkynyl, or optionally substituted aryl;

$R_6$ is H, optionally substituted $C_1$-$C_4$ alkyl, optionally substituted $C_2$-$C_4$ alkenyl, or optionally substituted $C_2$-$C_4$ alkynyl;

$R_7$ is H, optionally substituted $C_1$-$C_4$ alkyl, optionally substituted $C_2$-$C_4$ alkenyl, or optionally substituted $C_2$-$C_4$ alkynyl;

$R_9$ is H, optionally substituted $C_1$-$C_4$ alkyl, optionally substituted $C_2$-$C_4$ alkenyl, optionally substituted $C_2$-$C_4$ alkynyl, or optionally substituted aryl;

$R_{10}$ is H, CH$_2$N(CH$_3$)$_2$, CH$_2$N(CH$_2$CH$_3$)$_2$, CO$_2$R$_j$, where R$_j$ is optionally substituted $C_1$-$C_4$ alkyl, optionally substituted $C_2$-$C_4$ alkenyl, optionally substituted $C_2$-$C_4$ alkynyl, or optionally substituted aryl, CH$_2$OR$_i$, where R$_i$ is optionally substituted $C_1$-$C_4$ alkyl, optionally substituted $C_2$-$C_4$ alkenyl, optionally substituted $C_2$-$C_4$ alkynyl, or optionally substituted aryl, C(O)R$_h$, where R$_h$ is optionally substituted $C_1$-$C_4$ alkyl, optionally substituted $C_2$-$C_4$ alkenyl, optionally substituted $C_2$-$C_4$ alkynyl, or optionally substituted aryl, C(O)NHR$_g$, where R$_g$ is optionally substituted $C_1$-$C_4$ alkyl, optionally substituted $C_2$-$C_4$ alkenyl, optionally substituted $C_2$-$C_4$ alkynyl, or optionally substituted aryl, or CH$_2$NHR$_f$, where R$_f$ is optionally substituted $C_1$-$C_4$ alkyl, optionally substituted $C_2$-$C_4$ alkenyl, optionally substituted $C_2$-$C_4$ alkynyl, or optionally substituted aryl;

$R_{11}$ is H or C(O)R$_e$, where R$_e$ is optionally substituted $C_1$-$C_{20}$ alkyl, optionally substituted $C_2$-$C_{20}$ alkenyl, or optionally substituted $C_2$-$C_{20}$ alkynyl;

$R_{12}$ is H, optionally substituted morpholinyl, or OR$_k$, where R$_k$ is optionally substituted $C_1$-$C_4$ alkyl, optionally substituted $C_2$-$C_4$ alkenyl, optionally substituted $C_2$-$C_4$ alkynyl, or optionally substituted aryl; and,

- - - denotes an optional, additional C—C bond, resulting in either a C=C bond between, $C_1$-$C_2$, $C_2$-$C_3$, $C_6$-$C_{6a}$, $C_{6a}$-$C_7$, or $C_9$-$C_{10}$, with the provisos that when present between: (i) $C_{6a}$-$C_7$, $R_7$ is not present; (ii) $C_6$-$C_{6a}$, $R_7$ is not present and either $R_5$ or $R_6$ is not present, and, when present, $R_5$ is other than =O; (iii) $C_1$-$C_2$, $R_1$ is other than =O, =CHCN or =CHCO$_2$R$_z$, and $R_2$ is other than =O, =CHCN or =CHCO$_2$R$_w$; and, (iv) $C_2$-$C_3$, $R_2$ is other than =O, =CHCN or =CHCO$_2$R$_w$, and $R_3$ is other than =O, =CHCN or =CHCO$_2$R$_t$.

As generally defined above, $R_1$ is H, =O, =CHCN, =CHCO$_2$R$_z$, where R$_z$ is optionally substituted $C_1$-$C_4$ alkyl, optionally substituted $C_2$-$C_4$ alkenyl, or optionally substituted $C_2$-$C_4$ alkynyl, α-CN, α-OH, α-OR$_y$, where R$_y$ is optionally substituted $C_1$-$C_4$ alkyl, optionally substituted $C_2$-$C_4$ alkenyl, or optionally substituted $C_2$-$C_4$ alkynyl, α-NO$_2$, spiroepoxy, or C(O)R$_x$, where R$_x$ is optionally substituted $C_1$-$C_4$ alkyl, optionally substituted $C_2$-$C_4$ alkenyl, or optionally substituted $C_2$-$C_4$ alkynyl. In a preferred embodiment, $R_1$ is H.

As generally defined above, $R_2$ is H, =O, =CHCN, =CHCO$_2$R$_w$, where R$_w$ is optionally substituted $C_1$-$C_4$ alkyl, optionally substituted $C_2$-$C_4$ alkenyl, or optionally substituted $C_2$-$C_4$ alkynyl, α-CN, α-OH, α-OR$_v$, where R$_v$ is optionally substituted $C_1$-$C_4$ alkyl, optionally substituted $C_2$-$C_4$ alkenyl, or optionally substituted $C_2$-$C_4$ alkynyl, α-NO$_2$, spiroepoxy, or C(O)R$_u$, where R$_u$ is optionally substituted $C_1$-$C_4$ alkyl, optionally substituted $C_2$-$C_4$ alkenyl, or optionally substituted $C_2$-$C_4$ alkynyl. In a preferred embodiment, $R_2$ is H. In another preferred embodiment, $R_2$ is =O.

As generally defined above, $R_3$ is H, =O, =CHCN, =CHCO$_2$R$_t$, where R$_t$ is optionally substituted $C_1$-$C_4$ alkyl, optionally substituted $C_2$-$C_4$ alkenyl, or optionally substituted $C_2$-$C_4$ alkynyl, —CN, α-OH, α-$OR_s$, where $R_s$ is optionally substituted $C_1$-$C_4$ alkyl, optionally substituted $C_2$-$C_4$ alkenyl, or optionally substituted $C_2$-$C_4$ alkynyl, α-$NO_2$, spiroepoxy, or $C(O)R_r$, where $R_r$ is optionally substituted $C_1$-$C_4$ alkyl, optionally substituted $C_2$-$C_4$ alkenyl, or optionally substituted $C_2$-$C_4$ alkynyl. In certain embodiments, $R_3$ is =O. In other certain embodiments, $R_3$ is spiroepoxy. In yet other certain embodiments, $R_3$ is α-CN. In other certain embodiments, $R_3$ is H. In one embodiment, a double bond is present between $C_2$-$C_3$ and $R_3$ is —CN.

As generally defined above, $R_4$ is H, optionally substituted $C_1$-$C_4$ alkyl, optionally substituted $C_2$-$C_4$ alkenyl, or optionally substituted $C_2$-$C_4$ alkynyl. In a preferred embodiment, $R_4$ is methyl. $R_4$ is in the alpha configuration.

As generally defined above, $R_5$ is H, =O, $NH(CH_3)_2$, $NH(CH_2CH_3)_2$, $CH_2N(CH_3)_2$, $CH_2N(CH_2CH_3)_2$, $CO_2R_q$, where $R_q$ is optionally substituted $C_1$-$C_4$ alkyl, optionally substituted $C_2$-$C_4$ alkenyl, optionally substituted $C_2$-$C_4$ alkynyl, or optionally substituted aryl, $CH_2OR_p$, where $R_p$ is optionally substituted $C_1$-$C_4$ alkyl, optionally substituted $C_2$-$C_4$ alkenyl, optionally substituted $C_2$-$C_4$ alkynyl, or optionally substituted aryl, $C(O)R_o$, where $R_o$ is optionally substituted $C_1$-$C_4$ alkyl, optionally substituted $C_2$-$C_4$ alkenyl, optionally substituted $C_2$-$C_4$ alkynyl, or optionally substituted aryl, $C(O)NHR_n$, where $R_n$ is optionally substituted $C_1$-$C_4$ alkyl, optionally substituted $C_2$-$C_4$ alkenyl, optionally substituted $C_2$-$C_4$ alkynyl, or optionally substituted aryl, $CH_2NHR_m$, where $R_m$ is optionally substituted $C_1$-$C_4$ alkyl, optionally substituted $C_2$-$C_4$ alkenyl, optionally substituted $C_2$-$C_4$ alkynyl, or optionally substituted aryl, or $OR_l$, where $R_l$ is optionally substituted $C_1$-$C_4$ alkyl, optionally substituted $C_2$-$C_4$ alkenyl, optionally substituted $C_2$-$C_4$ alkynyl, or optionally substituted aryl. In certain embodiments, the optionally substituted aryl is optionally substituted phenyl or naphthyl. In a preferred embodiment, $R_5$ is H.

As generally defined above, $R_6$ is H, optionally substituted $C_1$-$C_4$ alkyl, optionally substituted $C_2$-$C_4$ alkenyl, or optionally substituted $C_2$-$C_4$ alkynyl. In a preferred embodiment, $R_6$ is H.

As generally defined above, $R_7$ is H, optionally substituted $C_1$-$C_4$ alkyl, optionally substituted $C_2$-$C_4$ alkenyl, or optionally substituted $C_2$-$C_4$ alkynyl. In a preferred embodiment, $R_7$ is H. In certain embodiments, $R_7$ is in the beta configuration.

As generally defined above, $R_9$ is H, optionally substituted $C_1$-$C_4$ alkyl, optionally substituted $C_2$-$C_4$ alkenyl, optionally substituted $C_2$-$C_4$ alkynyl, or optionally substituted aryl. In other certain embodiments, the optionally substituted alkyl is optionally substituted alkyl aryl, such as alkyl benzyl. In a preferred embodiment, $R_9$ is H. $R_9$ is in the alpha configuration.

As generally defined above, $R_{10}$ is H, $CH_2N(CH_3)_2$, $CH_2N(CH_2CH_3)_2$, $CO_2R_j$, where $R_j$ is optionally substituted $C_1$-$C_4$ alkyl, optionally substituted $C_2$-$C_4$ alkenyl, optionally substituted $C_2$-$C_4$ alkynyl, or optionally substituted aryl, $CH_2OR_i$, where $R_i$ is optionally substituted $C_1$-$C_4$ alkyl, optionally substituted $C_2$-$C_4$ alkenyl, optionally substituted $C_2$-$C_4$ alkynyl, or optionally substituted aryl, $C(O)R_h$, where $R_h$ is optionally substituted $C_1$-$C_4$ alkyl, optionally substituted $C_2$-$C_4$ alkenyl, optionally substituted $C_2$-$C_4$ alkynyl, or optionally substituted aryl, $C(O)NHR_g$, where $R_g$ is optionally substituted $C_1$-$C_4$ alkyl, optionally substituted $C_2$-$C_4$ alkenyl, optionally substituted $C_2$-$C_4$ alkynyl, or optionally substituted aryl, or $CH_2NHR_f$, where $R_f$ is optionally substituted $C_1$-$C_4$ alkyl, optionally substituted $C_2$-$C_4$ alkenyl, optionally substituted $C_2$-$C_4$ alkynyl, or optionally substituted aryl. In other certain embodiments, the optionally substituted aryl is optionally substituted phenyl or naphthyl. In a preferred embodiment, $R_{10}$ is H. $R_{10}$ is in the alpha configuration.

As generally defined above, $R_{11}$ is H or $C(O)R_e$, where $R_e$ is optionally substituted $C_1$-$C_{20}$ alkyl, optionally substituted $C_2$-$C_{20}$ alkenyl, or optionally substituted $C_2$-$C_{20}$ alkynyl. In one embodiment, $R_e$ is optionally substituted $C_1$-$C_{15}$ alkyl, preferably optionally substituted $C_1$-$C_{10}$ alkyl, more preferably optionally substituted $C_1$-$C_4$ alkyl. In another embodiment, $R_e$ is optionally substituted $C_1$-$C_{15}$ alkenyl, preferably optionally substituted $C_1$-$C_{10}$ alkenyl, more preferably optionally substituted $C_1$-$C_4$ alkenyl. In yet another embodiment, $R_e$ is optionally substituted $C_1$-$C_{15}$ alkynyl, preferably optionally substituted $C_1$-$C_{10}$ alkynyl, more preferably optionally substituted $C_1$-$C_4$ alkynyl. In a preferred embodiment, $R_{11}$ is H.

As generally defined above, $R_{12}$ is H, optionally substituted morpholinyl, or $OR_k$, where $R_k$ is optionally substituted $C_1$-$C_4$ alkyl, optionally substituted $C_2$-$C_4$ alkenyl, optionally substituted $C_2$-$C_4$ alkynyl, or optionally substituted aryl. In certain embodiments, the optionally substituted aryl is optionally substituted phenyl or naphthyl. In a preferred embodiment, $R_{12}$ is H. $R_{12}$ is in the alpha configuration.

As generally defined above, - - - denotes an optional, additional C—C bond, resulting in either a C=C bond between, $C_1$-$C_2$, $C_2$-$C_3$, $C_6$-$C_{6a}$, $C_{6a}$-$C_7$, or $C_9$-$C_{10}$, with the provisos that when present between: (i) $C_{6a}$-$C_7$, $R_7$ is not present; (ii) $C_6$-$C_{6a}$, $R_7$ is not present and either $R_5$ or $R_6$ is not present, and, when present, $R_5$ is other than =O; (iii) $C_1$-$C_2$, $R_1$ is other than =O, =CHCN or =$CHCO_2R_z$, and $R_2$ is other than =O, =CHCN or =$CHCO_2R_w$; and, (iv) $C_2$-$C_3$, $R_2$ is other than =O, =CHCN or =$CHCO_2R_w$, and $R_3$ is other than =O, =CHCN or =$CHCO_2R_t$.

In one embodiment, a double bond is present between $C_9$-$C_{10}$. In another embodiment, a double bond is present between $C_{6a}$-$C_7$. In yet another embodiment, a double bond is present between $C_6$-$C_{6a}$. When a double bond is present between either $C_{6a}$-$C_7$ or $C_6$-$C_{6a}$, $R_7$ is not present. Further, when a double bond is present between $C_6$-$C_{6a}$, either $R_5$ or $R_6$ is not present, and, when present, $R_5$ is other than =O.

In other certain embodiments, a double bond is present between $C_1$-$C_2$. When a double bond is present between $C_1$-$C_2$, $R_1$ is other than =O, =CHCN or =$CHCO_2R_z$, and $R_2$ is other than =O, =CHCN or =$CHCO_2R_w$. In other certain embodiments, a double bond is present between $C_2$-$C_3$. When a double bond is present between $C_2$-$C_3$, $R_2$ is other than =O, =CHCN or =$CHCO_2R_w$, and $R_3$ is other than =O, =CHCN or =$CHCO_2R_t$. In one embodiment, a double bond is present between $C_2$-$C_3$ and $R_3$ is —CN.

It is to be noted that the present disclosure contemplates and is intended to encompass all of the various combinations and permutations (i.e., combinations of substituent options, locations and stereochemical configurations) possible here.

For example, in various embodiments, compounds of the present disclosure have the formula of (II-a):

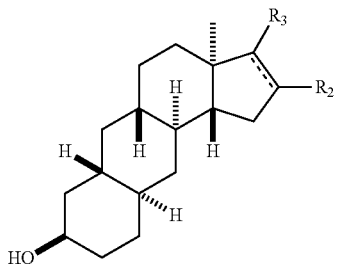

(II-a)

wherein:

$R_2$ is H, =O, =CHCN, =CHCO$_2$R$_w$, where R$_w$ is optionally substituted $C_1$-$C_4$ alkyl, optionally substituted $C_2$-$C_4$ alkenyl, or optionally substituted $C_2$-$C_4$ alkynyl, α-CN, α-OH, α-OR$_v$, where R$_v$ is optionally substituted $C_1$-$C_4$ alkyl, optionally substituted $C_2$-$C_4$ alkenyl, or optionally substituted $C_2$-$C_4$ alkynyl, α-NO$_2$, spiroepoxy, or C(O)R$_u$, where R$_u$ is optionally substituted $C_1$-$C_4$ alkyl, optionally substituted $C_2$-$C_4$ alkenyl, or optionally substituted $C_2$-$C_4$ alkynyl; and, $R_3$ is H, =O, =CHCN, =CHCO$_2$R$_t$, where R$_t$ is optionally substituted $C_1$-$C_4$ alkyl, optionally substituted $C_2$-$C_4$ alkenyl, or optionally substituted $C_2$-$C_4$ alkynyl, —CN, α-OH, α-OR$_s$, where R$_s$ is optionally substituted $C_1$-$C_4$ alkyl, optionally substituted $C_2$-$C_4$ alkenyl, or optionally substituted $C_2$-$C_4$ alkynyl, α-NO$_2$, spiroepoxy, or C(O)R$_r$, where R$_r$ is optionally substituted $C_1$-$C_4$ alkyl, optionally substituted $C_2$-$C_4$ alkenyl, or optionally substituted $C_2$-$C_4$ alkynyl; and,

- - - denotes an optional C—C bond, resulting in a C=C bond between $C_2$-$C_3$ with the proviso that when present, $R_2$ is other than =O, =CHCN, or =CHCO$_2$R$_w$ and, $R_3$ is other than =O, =CHCN or =CHCO$_2$R$_t$.

As generally defined above in Formula (II-a), $R_2$ is H, =O, =CHCN, =CHCO$_2$R$_w$, where R$_w$ is optionally substituted $C_1$-$C_4$ alkyl, optionally substituted $C_2$-$C_4$ alkenyl, or optionally substituted $C_2$-$C_4$ alkynyl, α-CN, α-OH, α-OR$_v$, where R$_v$ is optionally substituted $C_1$-$C_4$ alkyl, optionally substituted $C_2$-$C_4$ alkenyl, or optionally substituted $C_2$-$C_4$ alkynyl, α-NO$_2$, spiroepoxy, or C(O)R$_u$, where R$_u$ is optionally substituted $C_1$-$C_4$ alkyl, optionally substituted $C_2$-$C_4$ alkenyl, or optionally substituted $C_2$-$C_4$ alkynyl. In a preferred embodiment, $R_2$ is H. In another preferred embodiment, $R_2$ is =O.

As generally defined above in Formula (II-a), $R_3$ is H, =O, =CHCN, =CHCO$_2$R$_t$, where R$_t$ is optionally substituted $C_1$-$C_4$ alkyl, optionally substituted $C_2$-$C_4$ alkenyl, or optionally substituted $C_2$-$C_4$ alkynyl, —CN, α-OH, α-OR$_s$, where R$_s$ is optionally substituted $C_1$-$C_4$ alkyl, optionally substituted $C_2$-$C_4$ alkenyl, or optionally substituted $C_2$-$C_4$ alkynyl, α-NO$_2$, spiroepoxy, or C(O)R$_r$, where R$_r$ is optionally substituted $C_1$-$C_4$ alkyl, optionally substituted $C_2$-$C_4$ alkenyl, or optionally substituted $C_2$-$C_4$ alkynyl. In certain embodiments, $R_3$ is =O. In other certain embodiments, $R_3$ is spiroepoxy. In yet other certain embodiments, $R_3$ is α-CN. In other certain embodiments, $R_3$ is H.

As generally defined above in Formula (II-a), - - - denotes an optional C—C bond, resulting in a C=C bond between $C_2$-$C_3$. In one embodiment a double bond is present between $C_2$-$C_3$. When a double bond is present between $C_2$-$C_3$ in Formula (II-a), $R_3$ is —CN.

Accordingly, as noted, the cyclopent[a]anthracenes of Formulas (II) and (II-a) may encompass a number of various structures in accordance with the present disclosure, including all of the various combinations and permutations (i.e., combinations of substituent options, locations and stereochemical configurations) possible here.

Exemplary compounds of Formula (II) include, but are not limited to:

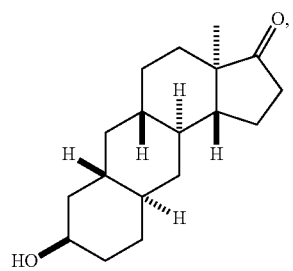

(MQ-64)

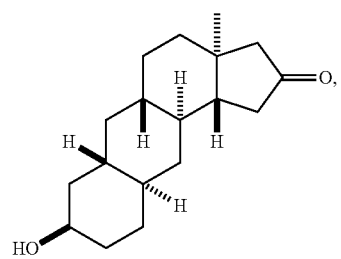

(MQ-65)

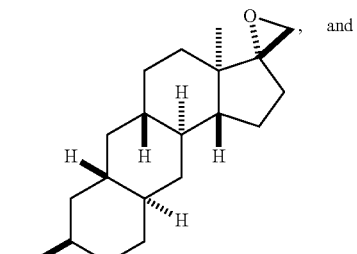

(MQ-81)

and

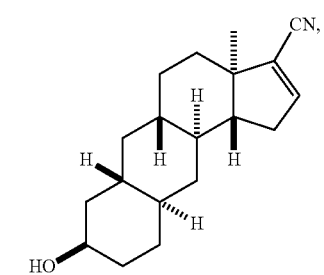

(MQ-82)

and pharmaceutically acceptable salts thereof.

In this regard it is to be noted that the structures provided above are of various exemplary embodiments. As such, they should not be viewed in a limiting sense.

2. Methods of Preparation and Pharmaceutical Compositions

It is to be noted that the compounds or cyclopent[a]anthracenes of the present disclosure, may in various embodiments be prepared or used in accordance with means generally known in the art. For example, in certain embodiments, the cyclopent[a]anthracenes of the present disclosure may be prepared or used in a pharmaceutically acceptable salt form. Suitable salt forms include, for example, citrate or chloride salt forms.

In various embodiments of the present disclosure, a pharmaceutical composition is disclosed that may comprise a cyclopent[a]anthracene or a combination of two or more thereof in accordance with the formulas of the present disclosure. The compounds or cyclopent[a]anthracenes of the present disclosure, as well as the various salt forms and other pharmaceutically acceptable forms, e.g., solvates and/or hydrates of compounds described herein, and pharmaceutical compositions containing them, may in general be prepared using methods and techniques known in the art, and/or as described in the Examples provided herein.

Without wishing to be bound by any particular theory, the compounds or cyclopent[a]anthracenes of the present disclosure are useful for potentiating GABA at $GABA_A$ receptors thereby inducing anesthesia or treating disorders related to GABA function (e.g., insomnia, mood disorders, Fragile X syndrome, convulsive disorders, anxiety disorders, or symptoms of ethanol withdrawal) in a subject, e.g., a human subject, and are preferably administered in the form of a pharmaceutical composition comprising an effective amount of a compound of the instant disclosure and optionally a pharmaceutically or pharmacologically acceptable carrier.

In one aspect, provided is a method of inducing anesthesia in a subject in need thereof, the method comprising administering to the subject a therapeutically effective amount of one or more of the above-noted cyclopent[a]anthracenes or pharmaceutically acceptable salts thereof, or a pharmaceutical composition thereof.

In another aspect, provided is a method of treating disorders related to GABA function in a subject in need thereof, the method comprising administering to the subject a therapeutically effective amount of one or more of the above-noted cyclopent[a]anthracenes or pharmaceutically acceptable salts thereof, or a pharmaceutical composition thereof. In certain embodiments, the disorder is selected from the group consisting of insomnia, mood disorders, convulsive disorders, Fragile X syndrome, anxiety, or symptoms of ethanol withdrawal.

In one embodiment of the present disclosure, a therapeutically effective amount of compound is from about 5 mg/kg to about 20 mg/kg, about 5 mg/kg to about 18 mg/kg, about 5 mg/kg to about 16 mg/kg, about 5 mg/kg to about 14 mg/kg, about 5 mg/kg to about 12 mg/kg, about 5 mg/kg to about 10 mg/kg, about 6 mg/kg to about 10 mg/kg, about 6 mg/kg to about 9 mg/kg, about 7 mg/kg to about 9 mg/kg, or about 8 mg/kg to about 16 mg/kg. In certain embodiments, a therapeutically effective amount of the compound is about 8 mg/kg. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The exact amount of a compound required to achieve an effective amount will vary from subject to subject, depending, for example, on species, age, and general condition of a subject, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations). In other certain embodiments, the compound may be administered via continuous intravenous (IV) infusion, such as used by those commonly skilled in the art of general anesthesia.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body.

The compound or composition can be administered concurrently with, prior to, or subsequent to, one or more additional therapeutically active agents. In general, each agent will be administered at a dose and/or on a time schedule determined for that agent. It will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. Exemplary therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

The pharmaceutical composition may also be in combination with at least one pharmacologically acceptable carrier. The carrier, also known in the art as an excipient, vehicle, auxiliary, adjuvant, or diluent, is any substance that is pharmaceutically inert, confers a suitable consistency or form to the composition, and does not diminish the therapeutic efficacy of the compounds. The carrier is "pharmaceutically or pharmacologically acceptable" if it does not produce an adverse, allergic, or other untoward reaction when administered to a mammal or human, as appropriate.

The pharmaceutical compositions containing the compounds or cyclopent[a]anthracenes of the present disclosure may be formulated in any conventional manner. Proper formulation is dependent upon the route of administration chosen. The compositions of the disclosure can be formulated for any route of administration, so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration. In certain embodiments, the route of administration is oral. In certain embodiments, the route of administration is parenteral. In certain embodiments, the route of administration is intravenous.

Pharmaceutically acceptable carriers for use in the compositions of the present disclosure are well known to those of ordinary skill in the art and are selected based upon a number of factors, including for example: the particular compound used, and its concentration, stability and intended bioavailability; the disease, disorder or condition being treated with the composition; the subject, its age, size and general condition; and/or the route of administration. Suitable carriers may be readily determined by one of ordinary skill in the art. (See, for example, J. G. Nairn, in: Remington's Pharmaceutical Science (A. Gennaro, ed.), Mack Publishing Co., Easton, Pa., (1985), pp. 1492-1517.)

The compositions may be formulated as tablets, dispersible powders, pills, capsules, gelcaps, caplets, gels, liposomes, granules, solutions, suspensions, emulsions, syrups, elixirs, troches, dragees, lozenges, or any other dosage form that can be administered orally. Techniques and compositions for making oral dosage forms useful in the present disclosure are described in the following exemplary references: 7 Modern Pharmaceutics, Chapters 9 and 10 (Banker & Rhodes, Editors, 1979); Lieberman et al., Pharmaceutical Dosage Forms: Tablets (1981); and, Ansel, Introduction to Pharmaceutical Dosage Forms 2nd Edition (1976).

The compositions of the present disclosure designed for oral administration comprise an effective amount of a compound of the disclosure in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques (e.g., to delay disintegration and absorption).

The compounds and cyclopent[a]anthracenes of the present disclosure may also be formulated for parenteral administration (e.g., formulated for injection via intravenous, intraarterial, subcutaneous, rectal, subcutaneous, intramuscular, intraorbital, intracapsular, intraspinal, intraperitoneal, or intrasternal routes). The compositions of the present disclosure for parenteral administration comprise an effective amount of the compound in a pharmaceutically acceptable carrier. Dosage forms suitable for parenteral administration include solutions, suspensions, dispersions, emulsions or any other dosage form that can be administered parenterally. Techniques and compositions for making parenteral dosage forms are known in the art. Typically formulations for parenteral administration are sterile or are sterilized before administration.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristate, fatty acid derived PEG esters such as PEG-hydroxyoleate and PEG-hydroxystearate, N-methyl pyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono-ricinoleate, polyoxyethylene sorbitan esters (such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del.), polyvinylpyrrolidone, alkyleneoxy modified fatty acid esters (such as polyoxyl 40 hydrogenated castor oil, cyclodextrins or modified cyclodextrins (e.g., beta-hydroxypropyl-cyclodextrin)), saccharide fatty acid esters (i.e., the condensation product of a monosaccharide (e.g., pentoses, such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzine; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the disclosure are well known to those of ordinary skill in the art, and are identified in The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, N.Y., 1995), The Pharmacological Basis of Therapeutics, (Goodman & Gilman, McGraw Hill Publishing), Pharmaceutical Dosage Forms, (H. Lieberman et al., eds.,) (Marcel Dekker, Inc., New York, N.Y., 1980), Remington's Pharmaceutical Sciences (A. Gennaro, ed., 19th ed.) (Mack Publishing, Easton, Pa., 1995), The United States Pharmacopeia 24, The National Formulary 19, (National Publishing, Philadelphia, Pa., 2000), A. J. Spiegel et al., and Use of Nonaqueous Solvents in Parenteral Products, J. of Pharm. Sciences, Vol. 52, No. 10, pp. 917-927 (1963).

Preferred solvents include cyclodextrins or modified cyclodextrins (e.g., beta-hydroxypropyl-cyclodextrin) as well as oils rich in triglycerides, for example, safflower oil, soybean oil or mixtures thereof, and alkyleneoxy modified fatty acid esters such as polyoxyl 40 hydrogenated castor oil. Commercially available triglycerides include Intralipid® emulsified soybean oil (Kabi-Pharmacia Inc., Stockholm, Sweden), Nutralipid® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®.

Additional minor components can be included in the compositions of the disclosure for a variety of purposes well known in the pharmaceutical industry. These components will for the most part impart properties which enhance retention of the compound at the site of administration, protect the stability of the composition, control the pH, facilitate processing of the compound into pharmaceutical formulations, and the like. Preferably, each of these components is individually present in less than about 15 wt % of the total composition, more preferably less than about 5 wt %, and most preferably less than about 0.5 wt % of the total composition. Some components, such as fillers or diluents, can constitute up to 90 wt % of the total composition, as is well known in the formulation art. Such additives include cryoprotective agents for preventing reprecipitation, surface active, wetting or emulsifying agents (e.g., lecithin, polysorbate-80, Tween® 80, Pluronic 60, polyoxyethylene stearate), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, cross-linked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

Dosage from administration by these routes may be continuous or intermittent, depending, for example, upon the patient's physiological condition, whether the purpose of the administration is therapeutic or prophylactic, and other factors known to and assessable by a skilled practitioner.

Those with ordinary skill in administering anesthetics can readily determine dosage and regimens for the administration of the pharmaceutical compositions of the disclosure or titrating to an effective dosage for use in treating insomnia, mood disorders, convulsive disorders, anxiety or symptoms of ethanol withdrawal. It is understood that the dosage of the compounds will be dependent upon the age, sex, health, and weight of the recipient, kind of concurrent treatment, if any, frequency of treatment, and the nature of the effect desired. For any mode of administration, the actual amount of compound delivered, as well as the dosing schedule necessary to achieve the advantageous effects described herein, will also depend, in part, on such factors as the bioavailability of the compound, the disorder being treated, the desired therapeutic dose, and other factors that will be apparent to those of skill in the art. The dose administered to an animal, particularly a human, in the context of the present disclosure should be sufficient to affect the desired therapeutic response in the animal over a reasonable period of time. Preferably, an effective amount of the compound, whether administered orally or by another route, is any amount that would result in a desired therapeutic response when administered by that route. The dosage may vary depending on the dosing schedule, which can be adjusted as necessary to achieve the desired therapeutic effect. The most preferred dosage will be tailored to the individual subject, as is understood and determinable by one of ordinary skill in the art without undue experimentation.

In one embodiment, solutions for oral administration are prepared by dissolving the compound in any pharmaceutically acceptable solvent capable of dissolving a compound (e.g., ethanol or methylene chloride) to form a solution. An appropriate volume of a carrier which is a solution, such as beta-hydroxypropyl-cyclodextrin, is added to the solution while stirring to form a pharmaceutically acceptable solution for oral administration to a patient. If desired, such solutions can be formulated to contain a minimal amount of, or to be free of, ethanol, which is known in the art to cause adverse physiological effects when administered at certain concentrations in oral formulations.

In another embodiment, powders or tablets for oral administration are prepared by dissolving a compound in any pharmaceutically acceptable solvent capable of dissolving the compound (e.g., ethanol or methylene chloride) to form a solution. The solvent can optionally be capable of evaporating when the solution is dried under vacuum. An additional carrier can be added to the solution prior to drying, such as beta-hydroxypropyl-cyclodextrin. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving a compound in any pharmaceutically acceptable solvent capable of dissolving the compound (e.g., ethanol or methylene chloride) to form a solution. An appropriate volume of a carrier which is an emulsion, such as Liposyn® II or Liposyn® III emulsions, is added to the solution while stirring to form a pharmaceutically acceptable emulsion for parenteral administration to a patient.

Solutions for parenteral administration can be prepared by dissolving a compound in any pharmaceutically acceptable solvent capable of dissolving the compound (e.g., ethanol or methylene chloride) to form a solution. An appropriate volume of a carrier which is a solution, such as beta-hydroxypropyl-cyclodextrin, is added to the solution while stirring to form a pharmaceutically acceptable solution for parenteral administration to a patient.

If desired, the emulsions or solutions described above for oral or parenteral administration can be packaged in IV bags, vials or other conventional containers in concentrated form and diluted with any pharmaceutically acceptable liquid, such as saline, to form an acceptable concentration prior to use as is known in the art.

Still further encompassed by the disclosure are kits (e.g., pharmaceutical packs). The kits provided may comprise a compound as described herein and a container (e.g., a vial, ampule, bottle, syringe, and/or dispenser package, or other suitable container). In some embodiments, provided kits may optionally further include a second container comprising a pharmaceutical carrier for dilution or suspension of the pharmaceutical composition or compound. In some embodiments, the pharmaceutical composition or compound provided in the container and the second container are combined to form one unit dosage form.

Optionally, instructions for use are additionally provided in such kits of the disclosure. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with an additional therapeutic agent.

3. Definitions

The term "steroid" as used herein describes an organic compound containing in its chemical nucleus the cyclopent[a]anthracene ring system.

As used herein, the terms "alpha" (α) and "beta" (β) are used to describe the absolute configuration and orientation of the structure so as to define the plane and which way up the molecule is represented. The term "alpha" refers to substituents below the plane and is shown by a broken line. The term "beta" refers to substituents above the plane and is shown by a solid, bolded line.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate and aryl sulfonate.

As used herein, a "subject" to which administration is contemplated includes, but is not limited to, mammals, e.g., humans (i.e., a male or female of any age group, e.g., a pediatric subject (e.g., child, adolescent) or adult subject (e.g., young adult, middle-aged adult or senior adult)), other primates (e.g., cynomolgus monkeys, rhesus monkeys) and commercially relevant mammals such as cattle, pigs, horses, sheep, goats, cats, and/or dogs. In any aspect and/or embodiment of the disclosure, the subject is a human.

As used herein, a "therapeutically effective amount" "an amount sufficient" or "sufficient amount" of a compound means the level, amount or concentration of the compound required for a desired biological response, e.g., analgesia.

The term "saturated" as used herein describes the state in which all available valence bonds of an atom (especially carbon) are attached to other atoms.

The term "unsaturated" as used herein describes the state in which not all available valence bonds along the alkyl chain are satisfied; in such compounds the extra bonds usually form double or triple bonds (chiefly with carbon).

When a range of values is listed, it is intended to encompass each value and sub-range within the range. For example "$C_{1-4}$ alkyl" is intended to encompass, $C_1$, $C_2$, $C_3$, $C_4$, $C_{1-3}$, $C_{1-2}$, $C_{2-4}$, $C_{2-3}$ and $C_{3-4}$ alkyl, while "$C_{1-22}$ alkyl" is intended to encompass, for example, $C_1$, $C_2$, $C_3$, $C_4$, etc., as well as $C_{1-21}$, $C_{1-20}$, $C_{1-15}$, $C_{1-10}$, $C_{2-20}$, $C_{2-15}$, $C_{2-10}$, $C_{3-15}$, $C_{3-10}$, etc. alkyl.

As used herein, "alkyl" refers to a radical of a straight-chain or branched saturated hydrocarbon group having from, in some embodiments, 1 to 4 carbon atoms ("$C_{1-4}$ alkyl"), and in other embodiments 1 to 22 carbon atoms ("$C_{1-22}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 4 carbon atom ("$C_{2-4}$ alkyl"). In yet other embodiments, an alkyl group has 1 to 21 carbon atoms ("$C_{1-21}$ alkyl"), 1 to 20 carbon atoms ("$C_{1-20}$ alkyl"), 1 to 15 carbon atoms ("$C_{1-15}$ alkyl"), 1 to 10 carbon atoms ("$C_{1-10}$ alkyl"), etc. Examples of such alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), pentyl ($C_5$), and the like.

As used herein, "alkenyl" or "alkene" refers to a radical of a straight-chain or branched hydrocarbon group having from, in some embodiments, 2 to 4 carbon atoms ("$C_{2-4}$ alkenyl"), and in other embodiments 2 to 22 carbon atoms ("$C_{2-22}$ alkenyl"), and one or more carbon-carbon double bonds. In some embodiments, an alkenyl group has 2 to 3 carbon atoms ("$C_{2-3}$ alkenyl"). In some embodiments, an alkenyl group has 2 carbon atoms ("$C_2$ alkenyl"). In yet other embodiments, an alkenyl group has 2 to 21 carbon atoms ("$C_{2-21}$ alkenyl"), 2 to 20 carbon atoms ("$C_{2-20}$ alkenyl"), 2 to 15 carbon atoms ("$C_{2-15}$ alkenyl"), 2 to 10 carbon atoms ("$C_{2-10}$ alkyl"), etc. The one or more carbon-carbon double bonds can be internal (such as in 2-butenyl) or terminal (such as in 1-butenyl). Examples of such alkenyl groups include ethenyl ($C_2$), 1-propenyl ($C_3$), 2-propenyl ($C_3$), 1-butenyl ($C_4$), 2-butenyl ($C_4$), butadienyl ($C_4$), 1-pentenyl ($C_5$), 2-pentenyl ($C_5$), and the like.

As used herein, "alkynyl" or "alkyne" refers to a radical of a straight-chain or branched hydrocarbon group having from 2 to 4 carbon atoms and one or more carbon-carbon triple bonds ("$C_{2-10}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like.

As used herein, "aryl" refers to a radical of a monocyclic or polycyclic (e.g., bicyclic or tricyclic) 4n+2 aromatic ring system (e.g., having 6, 10, or 14 electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl).

As used herein, "alkoxy" refers to an alkyl, alkenyl, or alkynyl group, as defined herein, attached to an oxygen radical.

Alkyl, alkenyl, alkynyl, and aryl groups, as defined herein, are substituted or unsubstituted, also referred to herein as "optionally substituted". In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that result in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary substituents include groups that contain a heteroatom (such as nitrogen, oxygen, silicon, phosphorous, boron, sulfur, or a halogen atom), halogen (e.g., chlorine, bromine, fluorine, or iodine), a heterocycle, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

EXAMPLES

The following Examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Example.

Compound Chemistry

In accordance with the following methods and Examples, the following compounds were prepared using methods known in the industry.

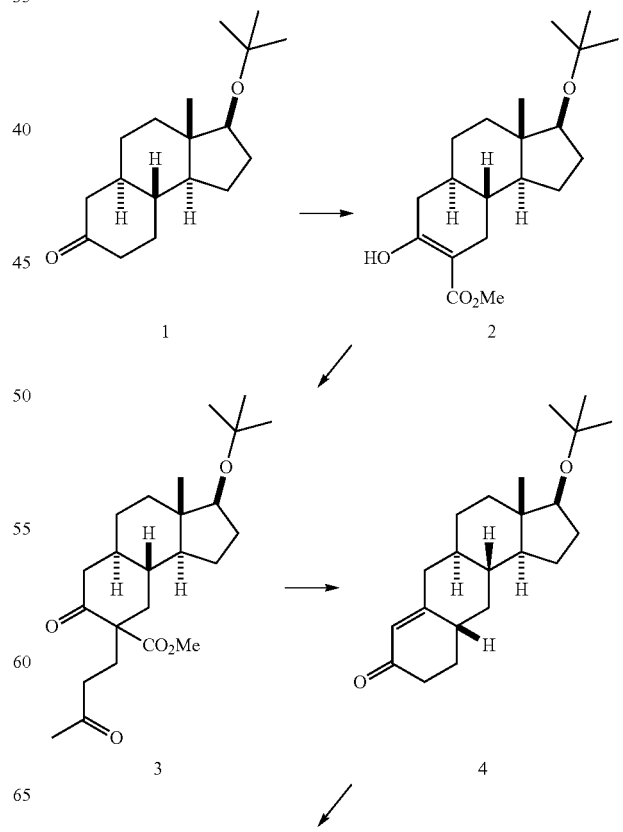

Scheme 1

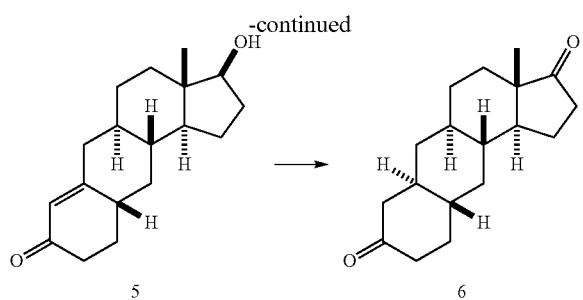

In accordance with Scheme 1, the following compounds were prepared using methods generally known in the art and as outlined below.

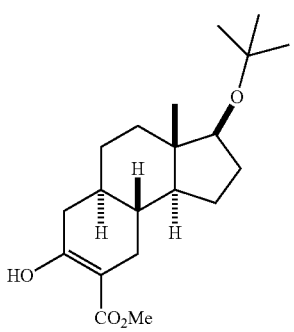

(3S,3aS,5aR,9aR,9bS)-3-(1,1-Dimethylethoxy)do-decahydro-3a-methyl-7H-Benz[e]inden-7-one (1)

Compound 1 was prepared as described previously (see Han, et al., "Neurosteroid Analogs. 3. The Synthesis and Electrophysiological Evaluation of Benz[e]indene Congeners of Neuroactive Steroids Having the 5â-Configuration," J. of Med. Chem., Vol. 38(22), pages 4548-56 (1995)).

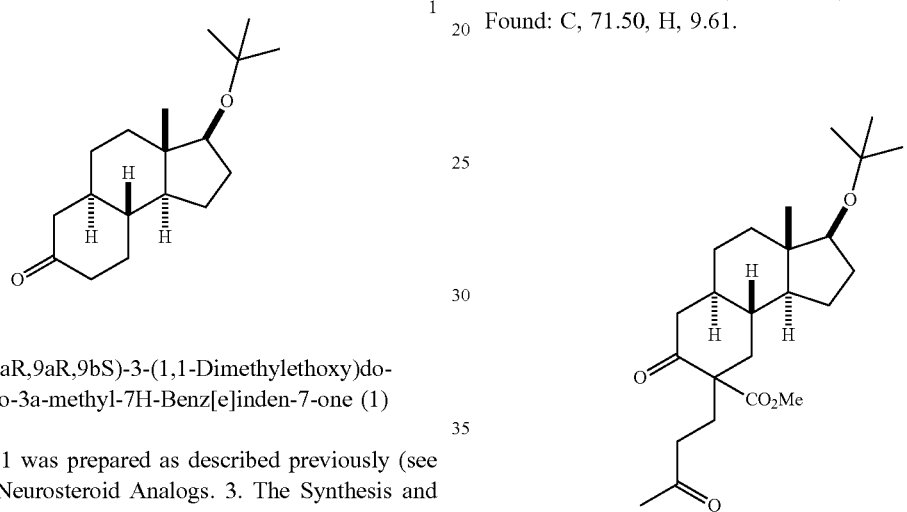

(3S,3aS,5aR,9aR,9bS)-2,3,3a,4,5,5a,6,9,9a,9b-Deca-hydro-3-(1,1-dimethylethoxy)-7-hydroxy-3a-methyl-1H-cyclopenta[a]naphthalene-8-carboxylic acid methyl ester (2)

Dimethyl carbonate (2.7 g, 30 mmol) was added to a suspension of sodium hydride (1.8 g, 60% in mineral oil, 45 mmol) in THF (50 mL) at room temperature. The mixture was refluxed for 30 min. Compound 1 (4.2 g, 15.7 mmol) in THF (20 mL) was added by syringe. The reaction was refluxed for 14 h and cooled to room temperature. Acetic acid was slowly added to the mixture until pH 4-5 and water (50 mL) was added. The product was extracted into EtOAc (100 mL×3) and the combined extracts were dried. The solution was filtered and solvents were removed under reduced pressure. The residue was purified by flash column chromatography (silica gel eluted with 5% EtOAc in hexanes) to afford compound 2 (3.6 g, 68%): [α]D25 −63.6 (c 0.42, CHCl3); 1H NMR (CDCl3) δ 12.10 (s, 1H), 3.71 (s, 3H), 3.39 (t, J=8.2 Hz, 1H), 1.11 (s, 9H), 0.72 (s, 3H); 13C NMR (CDCl3) δ 172.8, 171.6, 96.9, 80.6, 72.1, 51.3, 49.9, 42.9, 38.3, 36.9, 36.6, 36.1, 31.0, 28.7, 28.6, 28.5, 27.7, 23.5, 11.5. Anal. Calcd for (C20H32O4): C, 71.39; H, 9.59. Found: C, 71.50, H, 9.61.

(3S,3aS,5aR,9aR,9bS)-3-(1,1-Dimethylethoxy)do-decahydro-3a-methyl-7-oxo-8-(3-oxo-butyl)-cyclo-penta[a]naphthalene-8-carboxylic acid methyl ester (3)

Neutral alumina (6.0 g) was heated at 180° C. under high vacuum for 4 h. After cooling down to room temperature, the flask was charged with N2. Compound 2 (3.6 g, 6.5 mmol), vinyl methyl ketone (910 mg, 13 mmol), and CH2Cl2 (25 mL) were added to the anhydrous alumina at room temperature. The mixture was stirred at room temperature for 16 h. The suspension was filtered through Celite® 545 and washed with CH2Cl2 (50 mL×3). The solvent was removed under reduced pressure and the residue was purified by flash column chromatography (silica gel eluted with 10% EtOAc in hexanes) to afford diastereomeric 8R/8S product 3 (3.61 g, 95%, major/minor=10/1). The major diastereomer had: [α]D25 −80.7 (c 0.55, CHCl3); 1H NMR (CDCl3) δ 3.63 (s, 3H), 3.32 (t, J=8.2 Hz, 1H), 2.03 (s, 3H), 1.03 (s, 9H), 0.71 (s, 3H); 13C NMR (CDCl3) δ 208.4, 207.4, 172.7, 80.1, 72.0, 60.7, 51.9, 49.1, 44.9, 43.4, 43.1, 38.6, 38.3, 36.3, 35.1, 30.7, 29.8, 29.0, 28.5 (3C), 26.5, 23.2, 11.6. Anal. Calcd for (C24H38O5): C, 70.90; H, 9.42. Found: C, 70.72; H, 9.40.

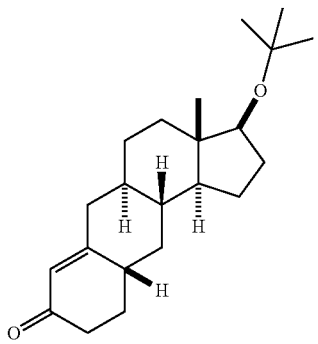

(3S,3aS,5aR,10aS,11aR,11bS)-1,2,3,3a,4,5,5a,6,9,
10,10a,11,11a,11b-Tetradecahydro-3-(1,1-dimethyl-
ethoxy)-3a-methyl-8H-Cyclopent[a]anthracen-8-one
(4)

Lithium chloride (1.53 g, 36 mmol) was added to compound 3 (3.6 g, 12.0 mmol) in anhydrous DMF (40 mL) at room temperature. The reaction was refluxed for 16 h and the solvent was removed under reduced pressure to afford the crude three ring decarboxylation product. The crude product was dissolved in EtOH (15 mL) and 0.5 N NaOH (15 mL) was added at room temperature. The reaction was refluxed and monitored by TLC. After 30 min, aqueous NH$_4$Cl was added. The product was extracted into EtOAc (100 mL×3) and dried. The solvent was filtered and removed under reduced pressure. The residue was purified by flash column chromatography (silica gel eluted with 10% EtOAc in hexanes) to afford compound 4 (2.1 g, 71%, two steps) as a colorless oil: $[\alpha]_D^{25}$ −6.8 (c 0.44, CHCl$_3$); $^1$H NMR (CDCl$_3$) δ 5.72 (s, 1H), 3.33 (t, J=8.2 Hz, 1H), 1.05 (s, 9H), 0.69 (s, 3H); $^{13}$C NMR (CDCl$_3$) δ 199.8, 166.5, 124.1, 80.3, 71.9, 49.4, 44.2, 42.9, 41.8, 40.2, 38.4, 37.4, 36.6, 36.5, 30.9, 29.0, 28.9, 28.5 (3C), 23.2, 11.5.

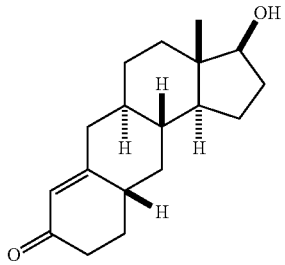

(3S,3aS,5aR,10aS,11aR,11bS)-1,2,3,3a,4,5,5a,6,9,
10,10a,11,11a,11b-Tetradecahydro-3-hydroxy-3a-
methyl-8H-Cyclopent[a]anthracen-8-one (5)

To a solution of compound 4 (2.05 g, 6.2 mmol) in MeOH (30 mL) was added 3 N HCl (30 mL) at room temperature. The reaction was stirred and refluxed for 4 h. After cooling to room temperature, the products were extracted into CH$_2$Cl$_2$ (50 mL×3), dried, filtered, and concentrated. The residue was purified by flash column chromatography (silica gel eluted with 20% EtOAc in hexanes) to give compound 5 (1.15 mg, 68%) as a white semisolid: $[\alpha]_D^{25}$ −30.5 (c 0.53, CHCl$_3$); $^1$H NMR (CDCl$_3$) δ 5.75 (s, 1H), 3.63 (t, J=8.2 Hz, 1H), 0.75 (s, 3H); $^{13}$C NMR (CDCl$_3$) δ 200.2, 166.8, 124.1, 81.3, 49.2, 44.1, 43.4, 41.8, 40.3, 38.4, 37.4, 36.5, 36.2, 30.0, 29.0, 28.9, 22.9, 11.1; IR $\nu_{max}$ 3420, 1659 cm$^{-1}$. Anal. Calcd for (C$_{18}$H$_{26}$O$_2$): C, 78.79; H, 9.55. Found: C, 78.61; H, 9.46.

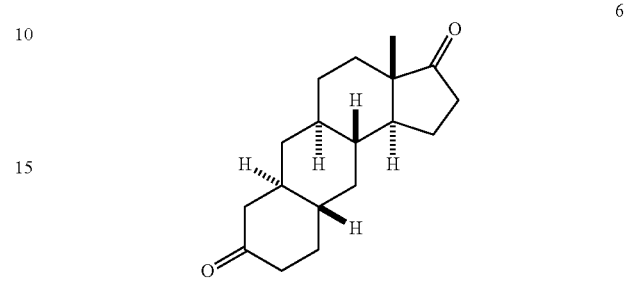

(3aS,5aR,6aR,10aS,11aR,11bS)-Tetradecahydro-3a-
methyl cyclopent[a]anthracene-3,8(2H,4H)-dione
(6)

A three-neck flask fitted with a dry ice condenser was cooled to −78° C., and anhydrous ammonia (100 mL) was condensed into the flask. Lithium (245 mg, 35 mmol) was added, and the resulting blue solution was stirred for 0.5 h. To this was added a solution of compound 5 (950 mg, 3.46 mmol) in dry THF (30 mL). After 3 h, solid NH$_4$Cl was added until the blue color disappeared and the flask was allowed to warm to room temperature overnight. Aqueous NH$_4$Cl was added and the product was extracted into EtOAc (100 mL×3). The combined extracts were washed with brine, dried and the solvent evaporated. The residue was dissolved in acetone (40 mL) and Jones reagent was added at 0° C. until a brown-yellowish color persisted. After 10 min, excess oxidant was consumed with by adding 2-propanol (1.0 mL). Brine (50 mL) was added and the product extracted into EtOAc (50 mL×3). The combined extracts were dried, filtered, and concentrated. The residue was purified by flash column chromatography (silica gel eluted with 20% EtOAc in hexanes) to give compound 6 (741 mg, 71%, 2 steps) as a white solid: mp 110-112° C., $[\alpha]_D^{25}$ +43.5 (c 0.37, CHCl$_3$); $^1$H NMR (CDCl$_3$) δ 0.83 (s, 3H); $^{13}$C NMR (CDCl$_3$) δ 220.7, 211.1, 50.1, 48.2, 48.1, 43.1, 43.0, 41.3, 41.1, 40.3, 40.2, 35.8, 35.6, 33.0, 31.3, 28.3, 21.3, 13.7; IR $\nu_{max}$ 1737, 1714 cm$^{-1}$. Anal. Calcd for (C$_{18}$H$_{26}$O$_2$): C, 78.79; H, 9.55. Found: C, 78.57; H, 9.40.

Scheme 2

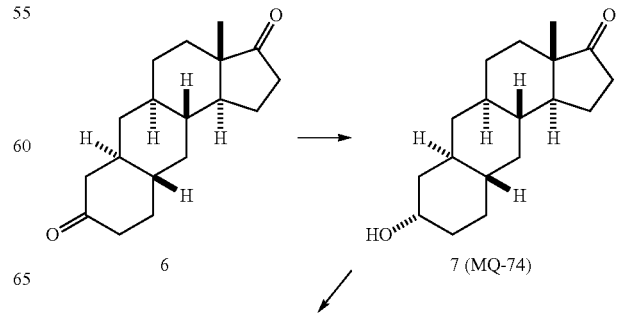

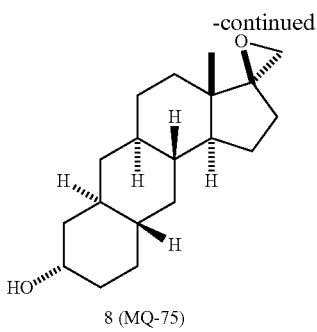

8 (MQ-75)

In accordance with Scheme 2, the following compounds were prepared using methods generally known in the art and as outlined below.

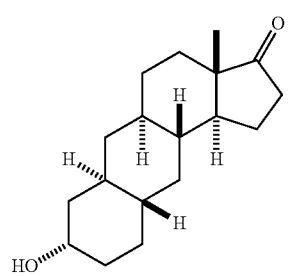

(3aS,5aR,6aR,8S,10aS,11aR,11bS)-Hexadecahydro-8-hydroxy-3a-methyl-cyclopent[a]anthracen-3-one (7)

To a solution of compound 6 (450 mg, 1.6 mmol) in THF (15 mL) was added K-selectride (2.0 mmol, 2.0 mL, 1.0 M in THF) at −78° C. After 3 h, 10% aqueous NaOH (15 mL) and 30% $H_2O_2$ (4 mL) were added at −78° C. After addition, the reaction was warmed up to room temperature for 1 h. The product was extracted into EtOAc (50 mL×3) and the combined extracts were dried, filtered, and concentrated. The residue was purified by flash column chromatography (silica gel, 30% EtOAc in hexanes) to give compound 7 (380 mg, 84%) as a white solid: mp 152-154° C., $[\alpha]_D^{25}$ +72.4 (c 0.39, CHCl$_3$); $^1$H NMR (CDCl$_3$) δ 4.08-4.06 (m, 1H), 0.85 (s, 3H); $^{13}$C NMR (CDCl$_3$) δ 221.3, 66.6, 50.3, 48.3, 44.2, 42.6, 40.7, 40.1, 40.0, 36.9, 36.2, 35.7, 32.8, 31.5, 28.7, 27.2, 21.5, 13.8; IR $\nu_{max}$ 3444, 1736 cm$^{-1}$. Anal. Calcd for (C$_{18}$H$_{28}$O$_2$): C, 78.21; H, 10.21. Found: C, 77.97; H, 10.06.

(MQ-75)

(2′S,3S,3aS,5aR,6aR,8S,10aS,11aR,11bS)-Hexadecahydro-3a-methyl-spiro[3H-cyclopent[a]anthracene-3,2′-oxiran]-8-ol (8)

To a solution of compound 7 (55 mg, 0.2 mmol) in DMF (3 mL) was added trimethylsulfonium iodide (204 mg, 1.0 mmol) and potassium tert-butoxide (112 mg, 1.0 mmol) at room temperature. After 3 h, water (20 mL) was added and the product extracted into EtOAc (50 mL×3). Solvents were dried, filtered, and concentrated. The residue was purified by flash column chromatography (silica gel eluted with 20% EtOAc in hexanes) to afford compound 8 (40 mg, 70%): mp 140-142° C.; $[\alpha]_D^{20}$ −10.7 (c 0.15, CHCl$_3$); $^1$H NMR (CDCl$_3$) δ 4.11-4.10 (m, 1H), 2.91 (s, J=5.1 Hz, 1H), 2.60 (s, J=5.1 Hz, 1H), 0.88 (s, 3H); $^{13}$C NMR (CDCl$_3$) δ 70.6, 66.9, 53.7, 51.7, 44.2, 42.8, 41.5, 40.8, 40.3, 40.1, 37.7, 36.3, 33.9, 32.9, 29.1, 29.0, 27.3, 23.2, 14.5; IR $\nu_{max}$ 3406, 1443 cm$^{-1}$. Anal. Calcd for (C$_{19}$H$_{30}$O$_2$): C, 78.57; H, 10.41. Found: C, 78.67; H, 10.24.

Scheme 3

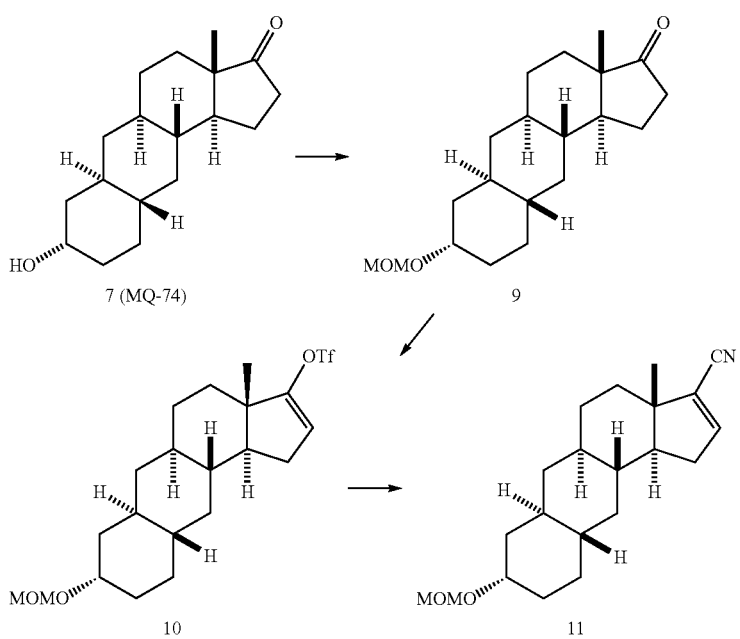

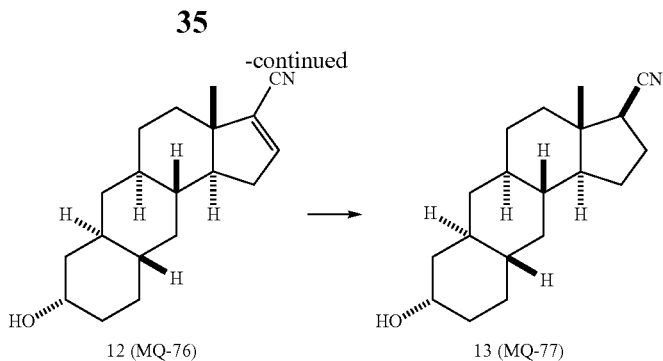

12 (MQ-76)    13 (MQ-77)

In accordance with Scheme 3, the following compounds were prepared using methods generally known in the art and as outlined below.

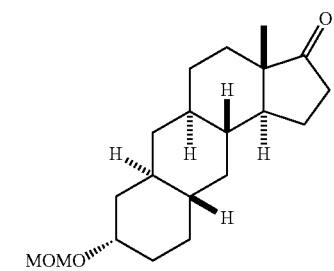

(3aS,5aR,6aR,8S,10aS,11aR,11bS)-Hexadecahydro-8-(methoxymethoxy)-3a-methyl-3H-cyclopent[a]anthracen-3-one (9)

To a solution of compound 8 (200 mg, 0.72 mmol) in dried dichloromethane (20 mL) was added DIPEA (260 mg, 2.0 mmol), chloromethyl methyl ether (121 mg, 1.5 mmol), and DMAP (10 mg) at room temperature. After 16 h, water was added and the product extracted into dichloromethane (100 mL×2). The combined extracts were dried, filtered, and removed. The residue was purified by flash column chromatography (silica gel eluted with 10% EtOAc in hexanes) to afford compound 9 (210 mg, 91%): $[\alpha]_D^{20}$ +43.9 (c 0.18, CHCl$_3$); $^1$H NMR (CDCl$_3$) δ 4.62 (s, 2H), 3.86 (s, br, 1H), 3.32 (s, 3H), 2.43 (dd, J=18.8 Hz, 8.6 Hz, 1H), 0.84 (s, 3H); $^{13}$C NMR (CDCl$_3$) δ 221.1, 94.5, 71.6, 55.0, 50.3, 48.3, 44.1, 42.5, 40.7, 40.2, 37.8, 36.9, 36.7, 35.7, 31.5, 30.3, 28.7, 27.8, 21.4, 13.8; IR $\nu_{max}$ 1738 cm$^{-1}$.

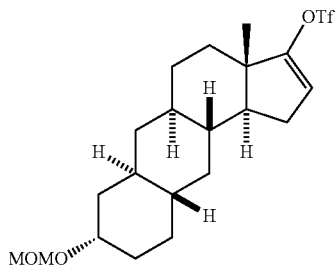

1,1,1-Trifluoromethanesulfonic acid (3aS,5aR,6aR,8S,10aS,11aR,11bS)-8-(methoxymethoxy)-3a-methyl-3a,4,5,5a,6,6a,7,8,9,10,10a,11,11a,11b tetradecahydro-1H-cyclopent[a]anthracen-3-yl ester (10)

To a solution of compound 9 (200 mg, 0.6 mmol) in THF (15 mL) was added potassium bis(trimethylsilyl) amide (0.5 M in toluene, 2.0 mL, 1.0 mmol) at −78° C. After 30 min, N-phenyltrifluoromethanesulfonimide (378 mg, 1.0 mmol) in 5 mL of THF was added at −78° C. After 2 h at −78° C., water was added and the product extracted into EtOAc (50 mL×3). The combined extracts were dried, filtered, and concentrated. The residue was purified by flash column chromatography (silica gel eluted with 10% EtOAc in hexanes) to afford compound 10 (350 mg) which was immediately converted in compound 11.

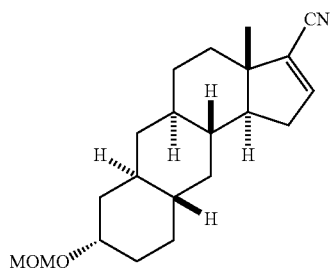

(3aS,5aR,6aR,8S,10aS,11aR,11bS)-8-(Methoxymethoxy)-3a-methyl-3a,4,5,5a,6,6a,7,8,9,10,10a,11,11a,11b-tetradecahydro-1H-cyclopent[a]anthracene-3-carbonitrile (11)

To compound 10 (350 mg) in a 50 mL flask was added sodium cyanide (150 mg, 3.0 mmol), copper (I) iodide (60 mg, 0.3 mmol) and Pd(PPh$_3$)$_4$ (30 mg) at room temperature. Acetonitrile (15 mL) was added and the reaction was refluxed for 1 h. Aqueous NH$_4$Cl was added and the product extracted into EtOAc (50 mL×3). The combined extracts were dried, filtered, and concentrated. The residue was purified by flash column chromatography (silica gel eluted with 10% EtOAc in hexanes) to afford compound 11 (203 mg containing an impurity from the sulfonimide reagent): $^1$H NMR (CDCl$_3$) δ 6.58 (s, 1H), 4.64 (s, 2H), 3.85 (s, br, 1H), 3.34 (s, 3H), 0.85 (s, 3H); $^{13}$C NMR (CDCl$_3$) δ 148.3, 127.0, 117.6, 94.3, 72.1, 55.1, 54.9, 48.8, 44.4, 42.4, 39.9, 39.6, 37.5, 37.5, 36.7, 33.8, 32.5, 30.1, 28.9, 27.6, 16.3; IR $\nu_{max}$ 3140, 2218 cm$^{-1}$.

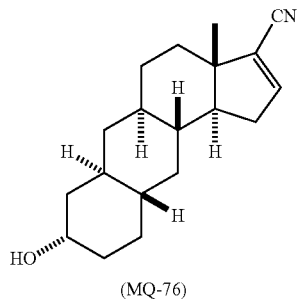

(MQ-76)

(3aS,5aR,6aR,8S,10aS,11aR,11bS)-8-Hydroxy-3a-methyl-3a,4,5,5a,6,6a,7,8,9,10,10a,11,11a,11b-Tetradecahydro-1H-cyclopent[a]anthracene-3-carbonitrile (12)

Compound 11 (203 mg with the impurity from the sulfonimide reagent) in methanol (10 mL) was added 6 N HCl (15 ml) at room temperature. After 14 h, the mixture was extracted into CH$_2$Cl$_2$ (50 mL×2). The combined extracts were dried, filtered, and concentrated. The residue was purified by flash column chromatography (silica gel eluted with 25% EtOAc in hexanes) to afford compound 12 (106 mg, 62% from compound 9): mp 164-166° C., $[\alpha]_D^{25}$ −16.0 (c 0.10, CHCl$_3$); $^1$H NMR (CDCl$_3$) δ 4.11 (s, br, 1H), 0.91 (s, 3H); $^{13}$C NMR (CDCl$_3$) δ 147.3, 127.6, 115.9, 66.7, 55.1, 48.8, 44.6, 42.7, 40.1, 40.0, 39.7, 37.9, 36.3, 33.9, 32.8, 32.5, 29.0, 27.2, 16.4; IR $v_{max}$ 3429, 2209, 1443 cm$^{-1}$. Anal. Calcd for (C$_{19}$H$_{27}$NO): C, 79.95; H, 9.53; N, 4.91. Found: C, 80.00; H, 9.39; N, 4.96.

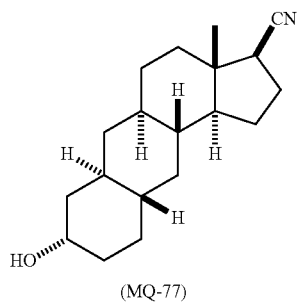

(MQ-77)

(3S,3aS,5aR,6aR,8S,10aS,11aR,11bS)-Hexadecahydro-8-hydroxy-3a-methyl-cyclopent[a]anthracene-3-carbonitrile (13)

To a solution of compound 12 (60 mg, 0.21 mmol) in EtOAc (40 mL) was added Pd/C (50 mg). Hydrogenation was carried out under 7 atm H$_2$ at room temperature for 3 h. The reaction mixture was filtered through Celite® 545 which was washed with EtOAc (100 mL). Solvents were removed and the residue was purified by flash column chromatography (silica gel eluted with 10% EtOAc in hexanes) to afford compound 13 (45 mg, 75%): 153-155° C.; $[\alpha]_D^{25}$ +28.2 (c 0.17, CHCl$_3$); $^1$H NMR (CDCl$_3$) δ 4.11-4.10 (m, 1H), 2.30 (t, J=9.2 Hz, 1H), 0.92 (s, 3H); $^{13}$C NMR (CDCl$_3$) δ 121.4, 66.8, 66.7, 53.2, 45.0, 43.8, 42.7, 41.6, 40.3, 40.0, 38.1, 37.1, 36.2, 32.9, 29.1, 27.2, 26.5, 24.2, 14.5; IR $v_{max}$ 3434, 2237, 1448 cm$^{-1}$. Anal. Calcd for (C$_{19}$H$_{29}$NO): C, 79.39; H, 10.17; N, 4.87. Found: C, 79.37; H, 10.16; N, 4.79.

Scheme 4

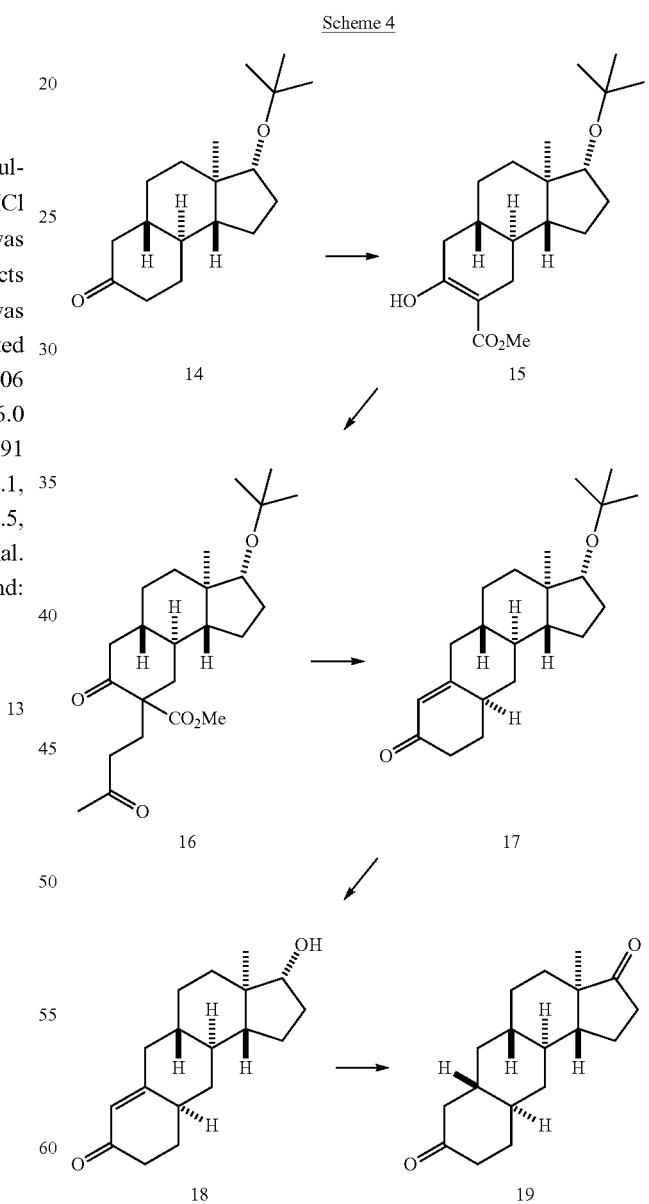

In accordance with Scheme 4, the following compounds were prepared using methods generally known in the art and as outlined below.

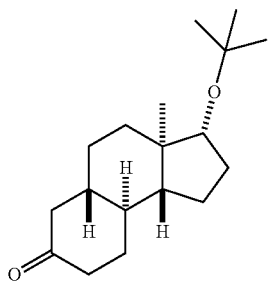

(3R,3aR,5aS,9aS,9bR)-3-(1,1-Dimethylethoxy)do-decahydro-3a-methyl-7H-Benz[e]inden-7-one (14)

Compound 14 was prepared as described previously (see Hu et al., "Neurosteroid analogs. Part 5. Enantiomers of neuroactive steroids and benz[e]indenes: total synthesis, electrophysiological effects on GABA receptor function and anesthetic actions in tadpoles," J. of the Chem. Soc., Perkin Transactions 1: Organic and Bio-Organic Chemistry, Vol. 24, pages 3665-3672 (1997)).

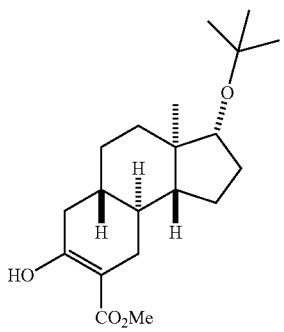

(3R,3aR,5aS,9aS,9bR)-2,3,3a,4,5,5a,6,9,9a,9b-Deca-hydro-3-(1,1-dimethylethoxy)-7-hydroxy-3a-methyl-1H-cyclopenta[a]naphthalene-8-carboxylic acid methyl ester (15)

Dimethyl carbonate (1.62 g, 18 mmol) was added to a suspension of sodium hydride (0.72 g, 60% in mineral oil, 18 mmol) in THF (50 mL) at room temperature. The mixture was refluxed for 30 min. Then compound 14 (2.4 g, 9 mmol) in THF (20 mL) was added by syringe. The reaction was refluxed for 14 h and cooled down to room temperature. Acetic acid was slowly added to the mixture until pH 4-5 and water (50 mL) was added. The products were extracted into EtOAc (100 mL×3) and the combined extracts were dried. The solution was filtered and solvents were removed under reduced pressure. The residue was purified by flash column chromatography (silica gel eluted with 5% EtOAc in hexanes) to afford compound 15 (2.1 g, 72%): $^1$H NMR (CDCl$_3$) δ 12.10 (s, 1H), 3.72 (s, 3H), 3.40 (t, J=7.7 Hz, 1H), 1.11 (s, 9H), 0.73 (s, 3H); $^{13}$C NMR (CDCl$_3$) δ 172.9, 171.6, 96.9, 80.7, 72.1, 51.2, 50.0, 42.9, 38.4, 37.0, 36.7, 36.2, 31.1, 28.7 (3C), 27.8, 23.6, 11.5. MS (FAB) for $[C_{20}H_{32}O_4+H]^+$: 337.2379. Found: 337.2379.

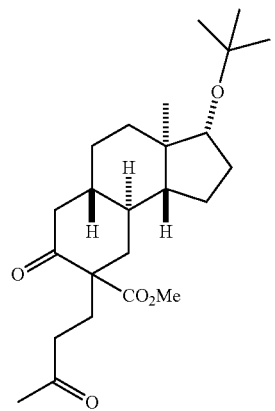

(3R,3aR,5aS,9aS,9bR)-3-(1,1-Dimethylethoxy)do-decahydro-3a-methyl-7-oxo-8-(3-oxo-butyl)-cyclopenta[a]naphthalene-8-carboxylic acid methyl ester (16)

Neutral alumina (4.0 g) was heated at 180° C. under high vacuum for 4 h. After cooling down to room temperature, the flask was filled with N$_2$. Compound 15 (2.1 g, 6.5 mmol), vinyl methyl ketone (910 mg, 13 mmol), and CH$_2$Cl$_2$ (20 mL) were added to the anhydrous alumina at room temperature. The mixture was stirred at room temperature for 16 h. The suspension was filtered through Celite® 545 which was washed with CH$_2$Cl$_2$ (50 mL×3). The solvent was removed under reduced pressure and the residue was purified by flash column chromatography (silica gel eluted with 10% EtOAc in hexanes) to afford diastereomeric 8R/8S product 16 (2.4 g, 95%, major/minor=7.5/1). The major diastereomer had: $^1$H NMR (CDCl$_3$) δ 3.97 (s, 3H), 3.32 (t, J=7.7 Hz, 1H), 2.02 (s, 3H), 1.02 (s, 9H), 0.70 (s, 3H); $^{13}$C NMR (CDCl$_3$) δ 208.3, 207.2, 172.7, 80.2, 72.0, 60.7, 51.9, 49.1, 45.0, 43.4, 43.1, 38.6, 38.3, 36.4, 35.2, 30.7, 29.7, 29.0, 28.5 (3C), 26.6, 23.2, 11.6. MS (FAB) for $[C_{24}H_{38}O_5+H]^+$: 407.2789. Found: 407.2794.

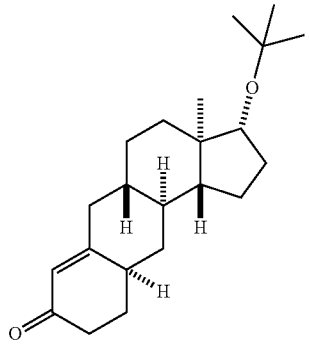

(3R,3aR,5aS,10aR,11aS,11bR)-1,2,3,3a,4,5,5a,6,9,10,10a,11,11a,11b-Tetradecahydro-3-(1,1-dimethylethoxy)-3a-methyl-8H-Cyclopent[a]anthracen-8-one (17)

Lithium chloride (1.02 g, 24 mmol) was added to compound 16 (2.4 g, 8.0 mmol) in anhydrous DMF (30 mL) at room temperature. The reaction was refluxed for 16 h and the solvent was removed under reduced pressure to afford the crude decarboxylation product. The crude product was dissolved in EtOH (15 mL) and 0.5 N NaOH (15 mL) was added at room temperature. The reaction was refluxed and monitored by TLC. After 30 min, aqueous NH$_4$Cl was added and the product was extracted into EtOAc (100 mL×3) and dried. The solvent was filtered and removed under reduced pressure. The residue was purified by flash column chromatography (silica gel eluted with 10% EtOAc in hexanes) to afford compound 17 (990 mg, 51%) as a colorless oil: $^1$H NMR (CDCl$_3$) δ 5.71 (s, 1H), 3.33 (t, J=7.7 Hz, 1H), 1.04 (s, 9H), 0.68 (s, 3H); $^{13}$C NMR (CDCl$_3$) δ 199.6, 166.4, 124.1, 80.4, 71.9, 49.3, 44.3, 42.9, 41.8, 40.2, 38.5, 37.4, 36.6, 36.4, 30.9, 29.1, 29.0, 28.5 (3C), 23.3, 11.5. MS (FAB) for [C$_{22}$H$_{34}$O$_2$+H]$^+$: 331.2637. Found: 331.2637.

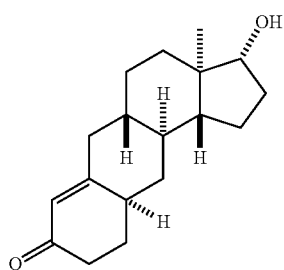

18

(3R,3aR,5aS,10aR,11aS,11bR)-1,2,3,3a,4,5,5a,6,9,10,10a,11,11a,11b-Tetradecahydro-3-hydroxy-3a-methyl-8H-Cyclopent[a]anthracen-8-one (18)

To compound 17 (990 mg, 3.0 mmol) in MeOH (20 mL) was added 3 N HCl (20 mL) at room temperature. The reaction was stirred and refluxed for 16 h. After cooling to room temperature, the product was extracted into CH$_2$Cl$_2$ (50 mL×3), dried, filtered, and concentrated. The residue was purified by flash column chromatography (silica gel eluted with 20% EtOAc in hexanes) to give compound 18 (680 mg, 83%) as a white semisolid: $^1$H NMR (CDCl$_3$) δ 5.71 (s, 1H), 3.59 (t, J=8.2 Hz, 1H), 0.70 (s, 3H); $^{13}$C NMR (CDCl$_3$) δ 200.1, 166.8, 124.0, 81.1, 49.3, 44.0, 43.3, 41.7, 40.2, 38.3, 37.3, 36.3, 36.1, 29.9, 28.9, 28.8, 22.8, 11.0. MS (FAB) for [C$_{18}$H$_{26}$O$_2$+Na]$^+$: 297.1830. Found: 297.1826.

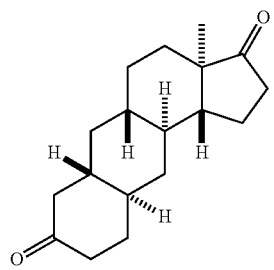

19

(3aR,5aS,6aS,9aR,10aR,11aS,11bR)-Tetradecahydro-3a-methyl-cyclopent[a]anthracene-3,8(2H,4H)-dione (19)

A three-neck flask fitted with a dry ice condenser was cooled to −78° C. and anhydrous ammonia (100 mL) was condensed into the flask. Lithium (0.14 g, 20 mmol) was added and the resulting blue solution was stirred for 0.5 h. To this was added a solution of compound 18 (650 mg, 2.35 mmol) in dry THF (30 mL). After 3 h, solid NH$_4$Cl was added until the blue color disappeared. The quenched reaction was allowed to warm to room temperature overnight. Aqueous NH$_4$Cl was added and the product was extracted into EtOAc (100 mL×3). The combined organic fractions were washed with brine, dried and the solvent evaporated. The residue was dissolved in acetone (40 mL) and Jones reagent was added at 0° C. until a brown-yellowish color persisted. After 10 min, excess oxidant was consumed with added 2-propanol (1.0 mL). Then, brine (50 mL) was added and the product extracted into EtOAc (50 mL×3). The combined extracts were dried, filtered, and concentrated. The residue was purified by flash column chromatography (silica gel eluted with 20% EtOAc in hexanes) to give compound 19 (453 mg, 70%) as a white solid: mp 111-113° C., [α]$_D^{25}$ −43.1 (c 0.26, CHCl$_3$); $^1$H NMR (CDCl$_3$) δ 0.82 (s, 3H); $^{13}$C NMR (CDCl$_3$) δ 220.4, 210.9, 50.1, 48.1, 48.0, 43.2, 43.0, 41.3, 41.1, 40.3, 40.2, 35.8, 35.5, 33.0, 31.3, 28.3, 21.3, 13.7; IR ν$_{max}$ 1737, 1713 cm$^{-1}$.

Scheme 5

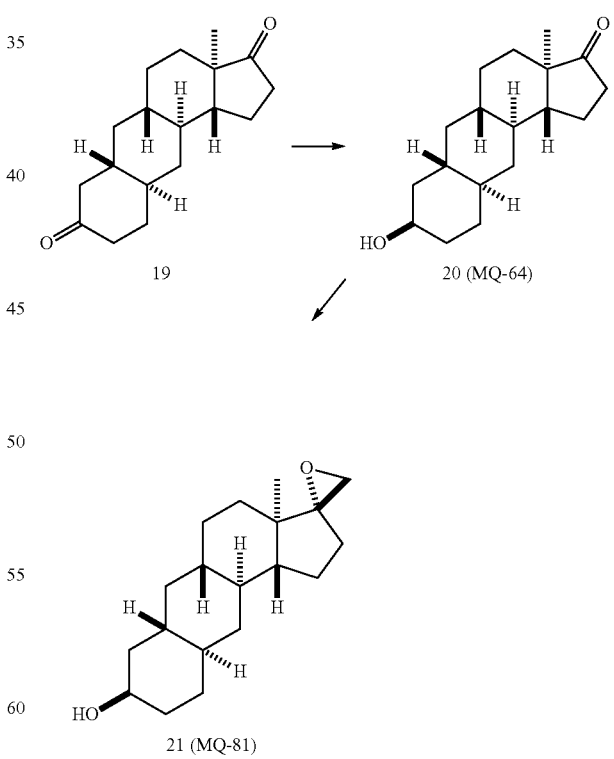

In accordance with Scheme 5, the following compounds were prepared using methods generally known in the art and as outlined below.

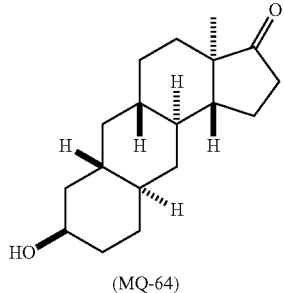

(MQ-64)

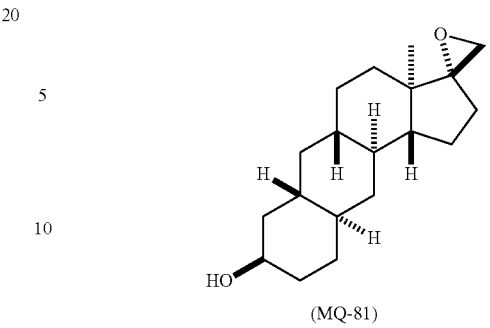

(MQ-81)

(3aR,5aS,6aS,8R,10aR,11aS,11bR)-Hexadecahydro-8-hydroxy-3a-methyl-3H-cyclopent[a]anthracen-3-one (20)

To a solution of compound 19 (240 mg, 0.87 mmol) in THF (10 mL) was added K-selectride (1.0 mmol, 1.0 mL, 1.0 M in THF) at −78° C. After 3 h, 10% of aqueous NaOH (10 mL) and 30% $H_2O_2$ (3 mL) were added at −78° C. After addition, the mixture was warmed up to room temperature for 1 h. The product was extracted into EtOAc (50 mL×3) and the combined extracts were dried, filtered, and concentrated. The residue was purified by flash column chromatography (silica gel eluted with 30% EtOAc in hexanes) to give compound 20 (180 mg, 75%) as a white solid: mp 152-154° C., $[\alpha]_D^{25}$ −72.9 (c 0.21, $CHCl_3$); $^1$H NMR ($CDCl_3$) δ 4.08-4.06 (m, 1H), 0.83 (s, 3H); $^{13}$C NMR ($CDCl_3$) δ 221.2, 66.6, 50.4, 48.3, 44.2, 42.6, 40.7, 40.1, 40.0, 36.9, 36.2, 35.7, 32.8, 31.5, 28.7, 27.2, 21.4, 13.8; IR $\nu_{max}$ 3424, 1736 $cm^{-1}$. Anal. Calcd for ($C_{18}H_{28}O_2$): C, 78.21; H, 10.21. Found: C, 78.60; H, 9.96.

(2′R,3R,3aR,5aS,6aS,8R,10aR,11aS,11bR)-Hexadecahydro-3a-methyl-spiro[3H-cyclopent[a]anthracene-3,2′-oxiran]-8-ol (21)

To a solution of compound 20 (42 mg, 0.16 mmol) in DMF (3 mL) was added trimethylsulfonium iodide (204 mg, 1.0 mmol) and potassium tert-butoxide (112 mg, 1.0 mmol) at room temperature. After 3 h, water (20 mL) was added and the product extracted into EtOAc (50 mL×3). Solvents were dried, filtered, and concentrated. The residue was purified by flash column chromatography (silica gel eluted with 20% EtOAc in hexanes) to afford compound 21 (31 mg, 71%): mp 143-145° C.; $[\alpha]_D^{20}$ +10.5 (c 0.18, $CHCl_3$); $^1$H NMR ($CDCl_3$) δ 4.11 (s, br, 1H), 2.91 (s, J=5.1 Hz, 1H), 2.60 (s, J=5.1 Hz, 1H), 0.89 (s, 3H); $^{13}$C NMR ($CDCl_3$) δ 70.6, 66.9, 53.7, 51.7, 44.2, 42.8, 41.5, 40.8, 40.3, 40.1, 37.7, 36.4, 33.9, 32.9, 29.1, 29.0, 27.3, 23.2, 14.5; IR $\nu_{max}$ 3400, 1443 $cm^{-1}$. Anal. Calcd for ($C_{19}H_{30}O_2$): C, 78.57; H, 10.41. Found: C, 78.34; H, 10.77.

Scheme 6

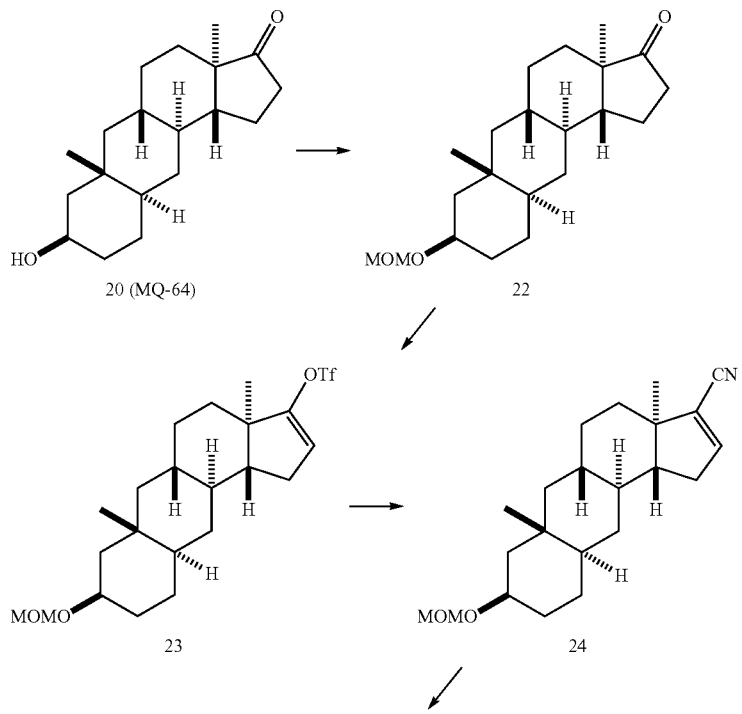

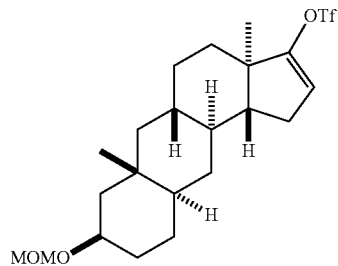

25 (MQ-82)

In accordance with Scheme 6, the following compounds were prepared using methods generally known in the art and as outlined below.

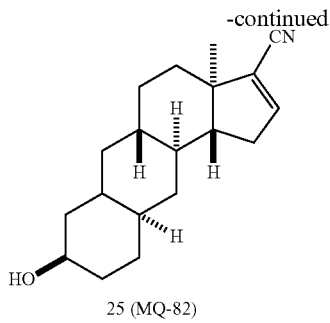

(3aR,5aS,6aS,8R,10aR,11aS,11bR)-Hexadecahydro-8-(methoxymethoxy)-3a-methyl-3H-cyclopent[a]anthracen-3-one (22)

To a solution of compound 21 (100 mg, 0.36 mmol) in dried dichloromethane (15 mL) was added DIPEA (130 mg, 1.0 mmol), chloromethyl methyl ether (121 mg, 1.5 mmol), and DMAP (10 mg) at room temperature. After 16 h, water was added and the product extracted into dichloromethane (100 mL×2). The combined extracts were dried, filtered, and solvent removed. The residue was purified by flash column chromatography (silica gel eluted with 10% EtOAc in hexanes) to afford compound 22 (116 mg, 100%): $^1$H NMR (CDCl$_3$) δ 4.61 (s, 2H), 3.86 (s, br, 1H), 3.32 (s, 3H), 2.42 (dd, J=19.2 Hz, 9.6 Hz, 1H), 0.84 (s, 3H); $^{13}$C NMR (CDCl$_3$) δ 221.1, 94.5, 71.6, 55.0, 50.3, 48.3, 44.2, 42.5, 40.7, 40.2, 37.8, 36.9, 36.7, 35.7, 31.5, 30.3, 28.7, 27.8, 21.5, 13.8; IR ν$_{max}$ 1739, 1041 cm$^{-1}$.

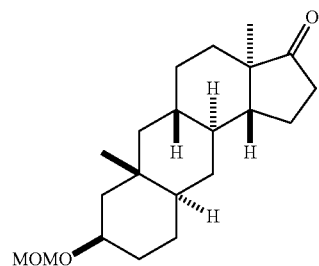

1,1,1-Trifluoromethanesulfonic acid (3aR,5aS,6aS,8R,10aR,11aS,11bR)-8-(methoxymethoxy)-3a-methyl-3a,4,5,5a,6,6a,7,8,9,10,10a,11,11a,11b-tetradecahydro-1H-cyclopent[a]anthracen-3-yl ester (23)

To a solution of compound 22 (96 mg, 0.3 mmol) in THF (15 mL) was added potassium bis(trimethylsilyl) amide (0.5 M in toluene, 1.0 mL, 0.5 mmol) at −78° C. After 30 min, the N-phenyltrifluoromethanesulfonimide (189 mg, 0.5 mmol) in 5 mL of THF was added at −78° C. After 2 h at −78° C., water was added and the product extracted into EtOAc (50 mL×3). The combined extracts were dried, filtered, and concentrated. The residue was purified by flash column chromatography (silica gel eluted with 10% EtOAc in hexanes) to afford compound 23 (200 mg with an impurity from the sulfonamide reagent) which was immediately converted to compound 24.

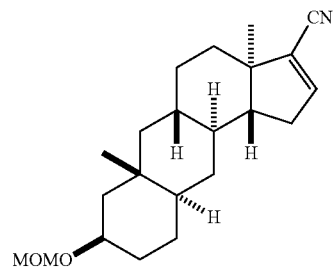

(3aR,5aS,6aS,8R,10aR,11aS,11bR)-8-(Methoxymethoxy)-3a-methyl-3a,4,5,5a,6,6a,7,8,9,10,10a,11,11a,11b-tetradecahydro-1H-cyclopent[a]anthracene-3-carbonitrile (24)

To compound 23 (185 mg with sulfonimide impurity) in a 50 mL round flask was added sodium cyanide (150 mg, 3.0 mmol), copper (I) iodide (60 mg, 0.3 mmol) and Pd(PPh$_3$)$_4$ (30 mg) at room temperature. Acetonitrile (15 mL) was added and the mixture was refluxed for 1 h. Aqueous NH$_4$Cl was added and the product extracted into EtOAc (50 mL×3). The combined extracts were dried, filtered, and concentrated. The residue was purified by flash column chromatography (silica gel eluted with 10% EtOAc in hexanes) to afford compound 24 (85 mg, 86% from compound 22): $^1$H NMR (CDCl$_3$) δ 6.61 (d, J=1.2 Hz, 1H), 4.65 (s, 2H), 3.90 (s, br, 1H), 3.36 (s, 3H), 0.92 (s, 3H); $^{13}$C NMR (CDCl$_3$) δ 147.2, 127.7, 115.9, 94.6, 71.7, 55.2, 48.8, 44.6, 42.6, 40.2, 39.8, 37.9, 37.8, 36.9, 34.0, 32.5, 30.4, 29.0, 27.8, 16.4; IR ν$_{max}$ 3396, 2209 cm$^{-1}$.

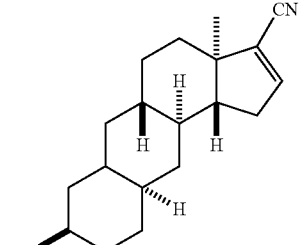

25 (MQ-82)

(3aR,5aS,6aS,8R,10aR,11aS,11bR)-8-Hydroxy-3a-methyl-3a,4,5,5a,6,6a,7,8,9,10,10a,11,11a,11b-Tetradecahydro-1H-cyclopent[a]anthracene-3-carbonitrile (25)

To compound 24 (83 mg, 0.25 mmol) in methanol (10 mL) was added 6 N HCl (10 ml) at room temperature. After 14 h, the mixture was extracted into CH$_2$Cl$_2$ (50 mL×2). The combined extracts were dried, filtered, and concentrated. The residue was purified by flash column chromatography (silica gel eluted with 25% EtOAc in hexanes) to afford compound 25 (38 mg, 53%): mp 165-167° C., $[\alpha]_D^{25}$ +16.2 (c 0.13, CHCl$_3$); $^1$H NMR (CDCl$_3$) δ 4.11 (s, br, 1H), 0.92 (s, 3H); $^{13}$C NMR (CDCl$_3$) δ 147.3, 127.6, 115.9, 66.7, 55.1, 48.8, 44.6, 42.7, 40.1, 40.0, 39.7, 37.9, 36.3, 33.9, 32.8, 32.5, 29.0, 27.7, 16.4; IR ν$_{max}$ 3376, 2213 cm$^{-1}$. Anal. Calcd for (C$_{19}$H$_{27}$NO): C, 79.95; H, 9.53; N, 4.91. Found: C, 80.06; H, 9.49; N, 4.95.

Scheme 7

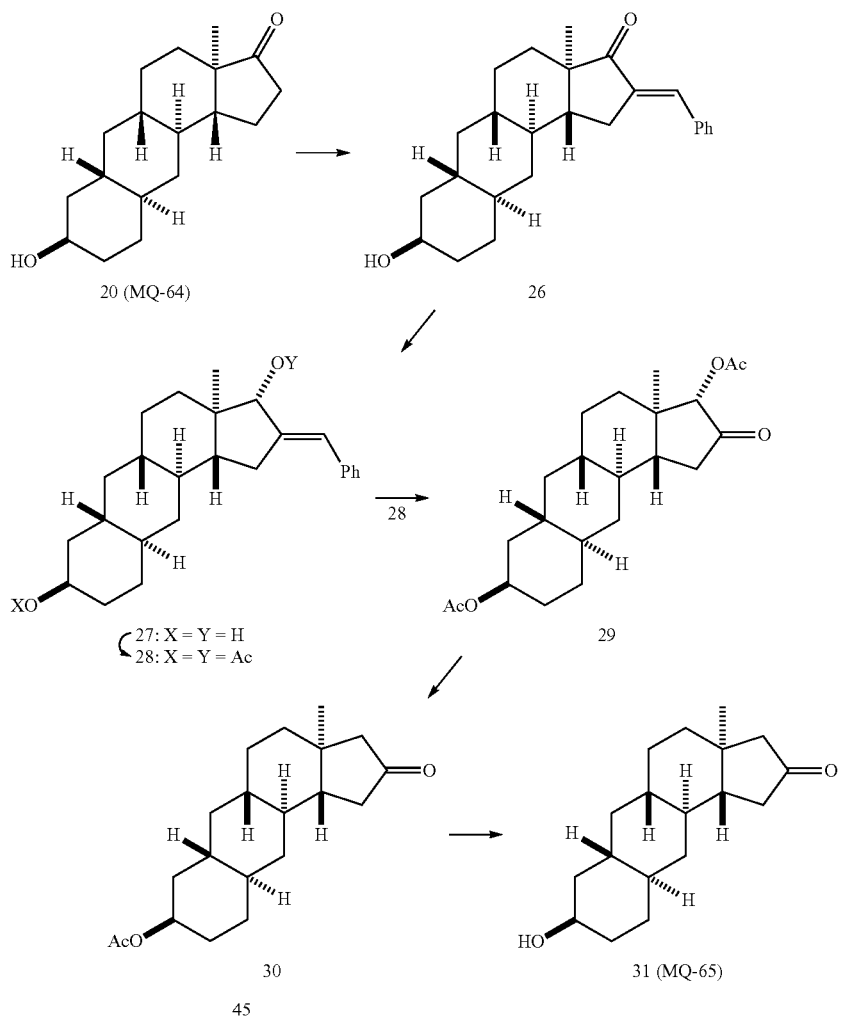

In accordance with Scheme 7, the following compounds were prepared using methods generally known in the art and as outlined below.

26

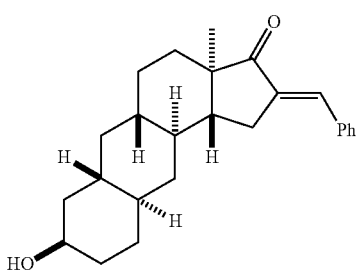

(2E,3aR,5aS,6aS,8R,10aR,11aS,11bR)-8-Hydroxy-3a-methyl-2-(phenylmethylene)-hexadecahydro-3H-cyclopent[a]anthracen-3-one (26)

To a solution of compound 25 (110 mg, 0.40 mmol) in ethanol (10 mL) was added benzaldehyde (86 mg, 0.8 mmol) and KOH (50 mg) at room temperature. After 16 h, aqueous NH₄Cl (50 mL) was added and the product was extracted into EtOAc (50 mL×3). Solvents were dried, filtered, and concentrated. The residue was purified by flash column chromatography (silica gel eluted with 20% EtOAc in hexanes) to give compound 26 (144 mg, 100%) as a white solid: ¹H NMR (CDCl₃) δ 7.45-7.21 (m, 6H), 5.12 (s, br, 1H), 4.06 (s, br, 1H), 0.87 (s, 3H); ¹³C NMR (CDCl₃) δ 209.9, 136.0, 135.5, 132.9, 130.1 (2C), 129.9, 128.5 (2C), 66.6, 48.3, 48.0, 44.2, 42.5, 40.2, 40.1, 39.8, 37.0, 36.0, 32.6, 31.5, 28.9, 28.7, 27.1, 14.4; IR $v_{max}$ 3356, 1716 cm⁻¹.

product extracted into dichloromethane (50 mL×3). Solvent was dried, filtered, and concentrated. The residue was purified by flash column chromatography (silica gel eluted with 25% EtOAc in hexanes) to give compound 28 (180 mg, 100%) as a white solid: ¹H NMR (CDCl₃) δ 7.39-7.09 (m, 5H), 6.13 (s, 1H), 5.32 (s, 1H), 5.00 (s, 1H), 2.63 (dd, J=16.7 Hz, 6.9 Hz, 1H), 2.13 (s, 3H), 1.98 (s, 3H), 0.72 (s, 3H); ¹³C NMR (CDCl₃) δ 171.1, 170.6, 140.9, 137.6, 130.0, 128.2 (3C), 126.4, 123.6, 84.5, 70.1, 47.8, 44.0, 43.5, 42.4, 40.6, 40.0, 37.6, 37.0, 36.9, 36.4, 30.6, 30.0, 29.0, 27.9, 21.4, 21.0, 12.3; IR $v_{max}$ 1733, 1241 cm⁻¹.

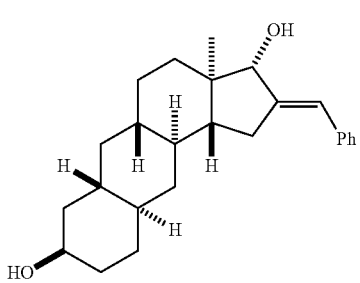

(2E,3R,3aR,5aS,6aS,8R,10aR,11aS,11bR)-3a-Methyl-2-(phenylmethylene)-hexadecahydro-cyclopent[a]anthracene-3,8-diol (27)

To a solution of compound 26 (144 mg, 0.36 mmol) in ethanol (20 mL) was added CeCl₃.7H₂O (559 mg, 1.5 mmol) and NaBH₄ (57 mg, 1.5 mmol) at 0° C. After 1 h, aqueous NH₄Cl (50 mL) was added and the product was extracted into EtOAc (50 mL×3). Solvents were dried, filtered, and concentrated. The residue was purified by flash column chromatography (silica gel eluted with 30% EtOAc in hexanes) to give compound 27 (145 mg, 100%) as a white solid: ¹H NMR (CDCl₃) δ 7.54-7.09 (m, 5H), 6.44-6.43 (m, 1H), 4.08-4.00 (m, 3H), 1.97 (s, 3H), 0.63 (s, 3H); ¹³C NMR (CDCl₃) δ 146.28, 138.1, 128.5 (2C), 128.4 (2C), 126.5, 123.1, 85.2, 67.1, 47.6, 44.6, 43.8, 43.0, 41.0, 40.5, 40.2, 38.0, 36.5, 33.0, 30.8, 29.4, 27.5, 11.4; IR $v_{max}$ 3345, 1692 cm⁻¹.

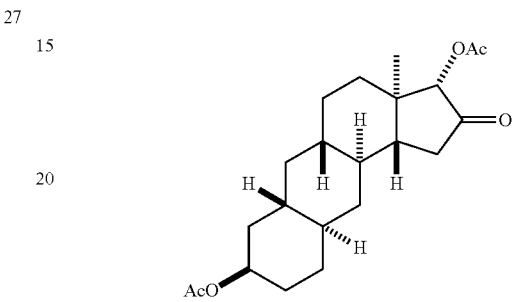

(3S,3aR,5aS,6aS,8R,10aR,11aS,11bR)-Hexadecahydro-3,8-dihydroxy-3a-methyl-2H-cyclopent[a]anthracen-2-one diacetate (29)

Compound 28 (180 mg, 0.34 mmol) was dissolved in methanol (40 mL) and EtOAc (20 mL) and cooled to −78° C. Ozone was bubbled through the solution for 30 min. Me₂S (5 mL) was added at −78° C. and the solution warmed up to room temperature for 16 h. Solvents were dried, filtered, and concentrated. The residue was purified by flash column chromatography (silica gel eluted with 20% EtOAc in hexanes) to give compound 29 (118 mg, 79%) as a white solid: ¹H NMR (CDCl₃) δ 5.02-5.00 (m, 2H), 2.10 (s, 3H), 1.99 (s, 3H), 0.78 (s, 3H); ¹³C NMR (CDCl₃) δ 210.7, 170.4, 170.1, 85.5, 69.9, 44.2, 43.9, 42.2, 42.1, 39.9, 37.6, 36.8, 36.7, 36.1, 35.7, 29.8, 28.4, 27.7, 21.3, 20.5, 12.3; IR $v_{max}$ 1762, 1734, 1240 cm⁻¹. MS (FAB) for [C₂₂H₃₂O₅+Na]⁺: 399.2147. Found: 399.2159.

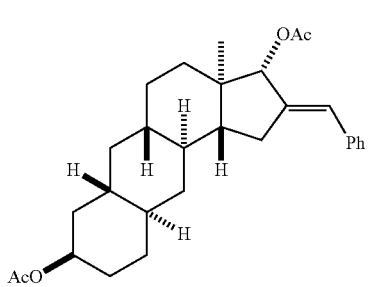

(2E,3R,3aR,5aS,6aS,8R,10aR,11aS,11bR)-3a-Methyl-2-(phenylmethylene)-hexadecahydro-cyclopent[a]anthracene-3,8-diol diacetate (28)

To a solution of compound 27 (145 mg, 0.4 mmol) in dichloromethane (10 mL) was added Ac₂O (102.1 mg, 1.0 mmol), Et₃N (151.8 mg, 1.5 mmol) and DMAP (5 mg) at room temperature. After 30 min, water was added and the

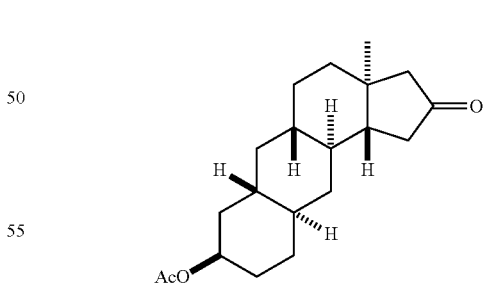

(3aS,5aS,6aS,8R,10aR,11aS,11bR)-8-Hydroxy-3a-methyl-hexadecahydro-2H-cyclopent[a]anthracen-2-one acetate (30)

Freshly prepared samarium filings (225 mg, 1.5 mmol) were added to THF (5 mL) followed by iodine (273 mg, 1.0 mmol) in THF (5 mL). The mixture was stirred under N₂ for 1 h until the mixture became a deep blue colored solution.

Compound 29 (115 mg, 0.306 mmol) in THF (9 mL) and methanol (0.2 mL) was added. After 1 h, aqueous Na$_2$CO$_3$ (30 mL) was added and the product was extracted into EtOAc (50 mL×3). Solvents were dried, filtered, and concentrated. The residue was purified by flash column chromatography (silica gel eluted with 20% EtOAc in hexanes) to give compound 30 (85 mg, 88%) as a white solid: $^1$H NMR (CDCl$_3$) δ 5.04-5.02 (m, 1H), 2.01 (s, 3H), 0.86 (s, 3H); $^{13}$C NMR (CDCl$_3$) δ 218.3, 170.4, 70.0, 55.9, 50.6, 44.0, 42.3, 40.6, 40.1, 39.6, 38.9, 38.3, 38.1, 37.0, 36.8, 29.9, 29.0, 27.8, 21.3, 18.1; IR ν$_{max}$ 1736, 1243 cm$^{-1}$; MS (FAB) for [C$_{20}$H$_{30}$O$_3$+H]$^+$: 319.2273, found: 319.2273.

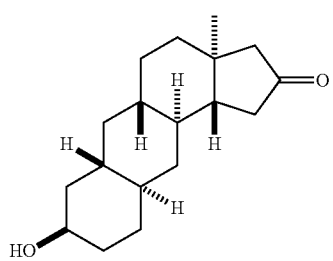

31 (MQ-65)

(3aS,5aS,6aS,8R,10aR,11aS,11bR)-8-Hydroxy-3a-methyl-hexadecahydro-2H-cyclopenta[a]anthracen-2-one (31)

To a solution of compound 30 (80 mg, 0.25 mmol) in methanol (20 mL) and water (1 mL) was added K$_2$CO$_3$ (500 mg, 3.6 mmol) at room temperature and the reaction was refluxed for 2 h. After cooling down to room temperature, brine (30 mL) was added and the product was extracted into EtOAc (50 mL×3). Solvents were dried, filtered and concentrated. The residue was purified by flash column chromatography (silica gel eluted with 30% EtOAc in hexanes) to give compound 31 (62 mg, 90%) as a white solid: mp 145-147° C.; [α]$_D^{25}$ +180.0 (c 0.28, CHCl$_3$); $^1$H NMR (CDCl$_3$) δ 4.08-4.07 (m, 1H), 0.86 (s, 3H); $^{13}$C NMR (CDCl$_3$) δ 218.7, 66.6, 55.9, 50.5, 44.1, 42.7, 40.7, 40.4, 39.9, 39.7, 38.9, 38.4, 38.0, 36.1, 32.8, 29.1, 27.2, 18.2; IR ν$_{max}$ 3436, 1741 cm$^{-1}$. Anal. Calcd for (C$_{18}$H$_{28}$O$_2$): C, 78.21; H, 10.21. Found: C, 78.26; H, 10.14.

[$^{35}$S]-TBPS Displacement

The IC$_{50}$ values for non-competitive displacers of [$^{35}$S]-TBPS from the picrotoxin binding site on GABA$_A$ receptors are reported in Table 1.

TABLE 1

Inhibition of [$^{35}$S]-TBPS Binding (nM)

| Compound | IC$_{50}$ | n$_{Hill}$ |
|---|---|---|
| MQ-74 | 1,190 ± 230 | 1.02 ± 0.15 |
| MQ-75 | 226 ± 2 | 1.99 ± 0.30 |
| MQ-76 | 574 ± 142 | 1.04 ± 0.22 |
| MQ-77 | 400 ± 118 | 0.88 ± 0.19 |
| MQ-64 | 346 ± 33 | 1.13 ± 0.10 |
| MQ-65 | 251 ± 66 | 0.78 ± 0.14 |
| MQ-81 | 174 ± 14 | 1.54 ± 0.16 |
| MQ-82 | 2,680 ± 520 | 1.09 ± 0.16 |

Results presented are from duplicate experiments performed in triplicate. Error limits are calculated as standard error of the mean. Methods used are known in the art (see Jiang, X., et al., Neurosteroid analogues. 9. Conformationally constrained pregnanes: structure-activity studies of 13,24-cyclo-18,21-dinorcholane analogues of the GABA modulatory and anesthetic steroids (3α,5α)- and (3α,5α)-3-hydroxypregnan-20-one. J. Med. Chem., 46: 5334-48 (2003)—the contents of which are hereby incorporated by reference in their entirety).

Electrophysiology Results

The compounds of the present disclosure were evaluated for the ability to potentiate chloride currents mediated by 2 μM GABA at rat α$_1$β$_2$γ$_{2L}$ type GABA$_A$ receptors expressed in *Xenopus laevis* oocytes and the results are shown in Table 2.

TABLE 2

Analogue Potentiation of GABA Effects at Rat α1β2γ2GABA$_A$ Receptors Expressed in Frog Oocytes

| Com-pound | Oocyte electrophysiology | | | |
|---|---|---|---|---|
| | 0.1 μM | 1.0 μM | 10 μM | (gating) 10 μM |
| MQ-74 | 0.80 ± 0.06 | 1.00 ± 0.0 | 3.88 ± 0.56 | −0.01 ± 0.04 |
| MQ-75 | 1.36 ± 0.03 | 7.67 ± 0.71 | 18.86 ± 1.99 | 0.13 ± 0.04 |
| MQ-76 | 0.95 ± 0.20 | 2.08 ± 0.16 | 9.43 ± 0.77 | 0.31 ± 0.30 |
| MQ-77 | 1.03 ± 0.10 | 3.65 ± 0.39 | 14.80 ± 1.53 | 0.02 ± 0.09 |
| MQ-64 | 0.98 ± 0.02 | 2.21 ± 0.17 | 8.81 ± 1.87 | 0.04 ± 0.03 |
| MQ-65 | 1.27 ± 0.04 | 2.94 ± 0.28 | 6.86 ± 1.34 | 0.02 ± 0.0 |
| MQ-81 | 1.37 ± 0.14 | 5.69 ± 0.17 | 18.39 ± 0.70 | 0.09 ± 0.01 |
| MQ-82 | 0.80 ± 0.04 | 0.83 ± 0.06 | 2.43 ± 0.34 | 0.19 ± 0.17 |

The GABA concentration used for the control response was 2 μM. Each compound was evaluated on at least four different oocytes at the concentrations indicated, and the results reported are the ratio of currents measured in the presence/absence of added compound. Gating represents direct current gated by 10 μM compound in the absence of GABA, and this current is reported as the ratio of compound only current/2 μM GABA current. Error limits are calculated as standard error of the mean (N≥4). Methods used are known in the art (see Jiang, X., et al.).

Tadpole Loss of Righting and Swimming

Table 3 discloses the anesthetic effects of the compounds of the present disclosure. In particular, the anesthetic effect of the compounds of the present disclosure on Loss of Righting Reflex (LRR) and Loss of Swimming Reflex (LSR).

TABLE 3

Tadpole Loss of Righting (LRR) & Loss of Swimming (LSR) EC$_{50}$ Values (μM) Reflexes by Analogues

| Com-pound | Tadpole LRR EC$_{50}$ (μM) | Tadpole LRR n$_{Hill}$ | Tadpole LSR EC$_{50}$ (μM) | Tadpole LSR n$_{Hill}$ |
|---|---|---|---|---|
| MQ-74 | 3.22 ± 0.03 | −15.6 ± 1.8 | >10 | — |
| MQ-75 | 0.26 ± 0.04 | −1.71 ± 0.42 | 0.95 ± 0.0 | −15.9 ± 0.5 |
| MQ-76 | 0.39 ± 0.01 | −2.31 ± 0.08 | 1.73 ± 0.03 | −36.3 ± 0.1 |
| MQ-77 | 0.59 ± 0.07 | −1.84 ± 0.31 | 1.73 ± 0.04 | −36.4 ± 0.1 |
| MQ-64 | 3.08 ± 0.01 | −15.5 ± 1.0 | None | — |
| MQ-65 | 2.09 ± 0.12 | −2.42 ± 0.24 | 5.48 ± 0.02 | −33.2 ± 0.2 |
| MQ-81 | 0.77 ± 0.04 | −2.94 ± 0.28 | 1.73 ± 0.04 | −36.4 ± 0.1 |
| MQ-82 | 3.11 ± 0.01 | −15.6 ± 1.1 | 7.93 ± 0.0 | −27.0 ± 0.0 |

Methods used are known in the art (see Jiang, X., et al.). Error limits are calculated as standard error of the mean (N=10 or more animals at each of five or more different concentrations).

General Methods

The compounds discussed in the present disclosure were produced as discussed elsewhere throughout this disclosure and by the following methods.

Solvents were either used as purchased or dried and purified by standard methodology. Extraction solvents were dried with anhydrous $Na_2SO_4$ and after filtration, removed on a rotary evaporator. Flash chromatography was performed using silica gel (32-63 μm) purchased from Scientific Adsorbents (Atlanta, Ga.). Melting points were determined on a Kofler micro hot stage and are uncorrected. FT-IR spectra were recorded as films on a NaCl plate. NMR spectra were recorded in $CDCl_3$ at ambient temperature at 300 MHz ($^1H$) or 74 MHz ($^{13}C$). Purity was determined by TLC on 250 μm thick Uniplates™ from Analtech (Newark, Del.). All pure compounds (purity >95%) gave a single spot on TLC. Elemental analyses were performed by M-H-W Laboratories (Phoenix, Ariz.).

EQUIVALENTS AND SCOPE

In view of the above, it will be seen that the several advantages of the disclosure are achieved and other advantageous results attained. As various changes could be made in the above processes and composites without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. It is also noted that the terms "comprising", "including", "having" or "containing" are intended to be open and permits the inclusion of additional elements or steps.

What is claimed is:

1. A compound of Formula (II-a):

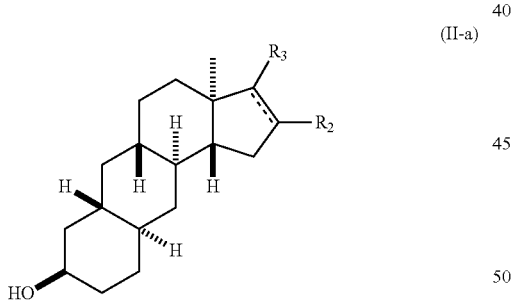

(II-a)

wherein $R_2$ is H, =O, =CHCN, =CHCO$_2$R$_w$, where R$_w$ is optionally substituted $C_1$-$C_4$ alkyl, optionally substituted $C_2$-$C_4$ alkenyl, or optionally substituted $C_2$-$C_4$ alkynyl, α-CN, α-OH, α-OR$_v$, where R$_v$ is optionally substituted $C_1$-$C_4$ alkyl, optionally substituted $C_2$-$C_4$ alkenyl, or optionally substituted $C_2$-$C_4$ alkynyl, α-NO$_2$, spiroepoxy, or C(O)R$_u$, where R$_u$ is optionally substituted $C_1$-$C_4$ alkyl, optionally substituted $C_2$-$C_4$ alkenyl, or optionally substituted $C_2$-$C_4$ alkynyl;

$R_3$ is H, =O, =CHCN, =CHCO$_2$R$_t$, where R$_t$ is optionally substituted $C_1$-$C_4$ alkyl, optionally substituted $C_2$-$C_4$ alkenyl, or optionally substituted $C_2$-$C_4$ alkynyl, —CN, α-OH, α-OR$_s$, where R$_s$ is optionally substituted $C_1$-$C_4$ alkyl, optionally substituted $C_2$-$C_4$ alkenyl, or optionally substituted $C_2$-$C_4$ alkynyl, α-NO$_2$, spiroe- poxy, or C(O)R$_r$, where R$_r$ is optionally substituted $C_1$-$C_4$ alkyl, optionally substituted $C_2$-$C_4$ alkenyl, or optionally substituted $C_2$-$C_4$ alkynyl; and,

- - - denotes an optional C—C bond, resulting in a C=C bond between $C_2$-$C_3$.

2. The compound of claim 1 having the structure:

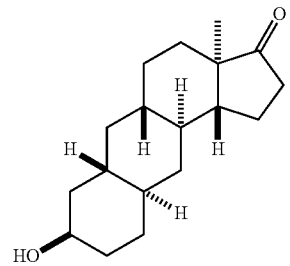

or a pharmaceutically acceptable salt thereof.

3. The compound of claim 1 having the structure:

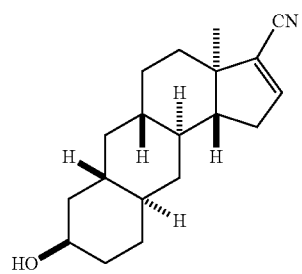

or a pharmaceutically acceptable salt thereof.

4. The compound of claim 1 having the structure:

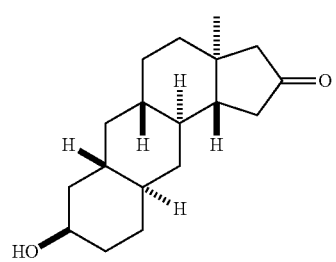

or a pharmaceutically acceptable salt thereof.

5. The compound of claim 1 having the structure:

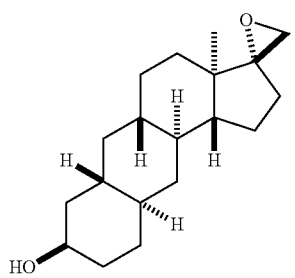

or a pharmaceutically acceptable salt thereof.

6. A method of inducing anesthesia in a subject in need thereof, said method comprising administering to the subject a therapeutically effective amount of a compound of claim 1, or a pharmaceutically acceptable salt thereof.

\* \* \* \* \*